(12) United States Patent
Takagi

(10) Patent No.: US 8,975,384 B2
(45) Date of Patent: Mar. 10, 2015

(54) TAG PEPTIDE AND USE THEREOF

(75) Inventor: Junichi Takagi, Suita (JP)

(73) Assignee: Osaka University, Osaka (JP)

( * ) Notice: Subject to any disclaimer, the term of this patent is extended or adjusted under 35 U.S.C. 154(b) by 783 days.

(21) Appl. No.: 12/864,343

(22) PCT Filed: Dec. 18, 2008

(86) PCT No.: PCT/JP2008/073069
§ 371 (c)(1),
(2), (4) Date: Sep. 15, 2010

(87) PCT Pub. No.: WO2009/096112
PCT Pub. Date: Aug. 6, 2009

(65) Prior Publication Data
US 2011/0039331 A1 Feb. 17, 2011

(30) Foreign Application Priority Data

Jan. 31, 2008 (JP) ................................. 2008-020804

(51) Int. Cl.
*C07K 1/22* (2006.01)
*C07K 7/06* (2006.01)
(Continued)

(52) U.S. Cl.
CPC ............ *C07K 5/1016* (2013.01); *G01N 33/543* (2013.01); *C07K 7/08* (2013.01);
(Continued)

(58) Field of Classification Search
CPC .......... C07K 1/22; C07K 5/1016; C07K 7/06; C07K 7/08; C07K 16/18; C07K 16/28; C07K 2317/55; C07K 2317/622; C07K 2317/92; C07K 2319/40; C07K 2319/60; G01N 33/531; G01N 33/543; G01N 33/68

USPC .......... 435/6.17, 7.1, 7.21, 69.3, 69.7, 70.21, 435/91.1, 331, 334, 320.1, 961, 975; 436/514, 518, 547, 548; 530/324, 325, 530/326, 327, 387.9, 388.22, 391.1, 413; 536/23.4, 23.5, 23.53

See application file for complete search history.

(56) References Cited

U.S. PATENT DOCUMENTS 6,111,075 A 8/2000 Xu et al.
2005/0272919 A1 12/2005 Duellman et al.

FOREIGN PATENT DOCUMENTS

CN 101004417 7/2007
WO 96/02641 1/1996
(Continued)

OTHER PUBLICATIONS

Brass et al., 1992. Structure and function of the human platelet thrombin receptor. J. Biol. Chem. 267: 13795-13798.*
(Continued)

*Primary Examiner* — Gail R Gabel
*Assistant Examiner* — James L Grun
(74) *Attorney, Agent, or Firm* — Wenderoth, Lind & Ponack, L.L.P.

(57) ABSTRACT

The present invention provides a tag peptide comprising an amino acid sequence represented by the following formula (I):

$$X_1\text{-Tyr-}X_2\text{-Gly-Gln-}X_3 \tag{I}$$

(wherein $X_1$, $X_2$ and $X_3$ are the same or different and each represent any amino acid residue) and an antibody against the tag peptide. By combined use of the tag peptide and antibody of the present invention, a system that enables proteins expressed from cloned genes to be highly purified in an inexpensive and easy manner can be established.

8 Claims, 21 Drawing Sheets

(51) Int. Cl.
*C07K 7/08* (2006.01)
*C07K 16/18* (2006.01)
*C07K 16/28* (2006.01)
*G01N 33/531* (2006.01)
*G01N 33/543* (2006.01)
*G01N 33/68* (2006.01)
*C07K 5/107* (2006.01)

(52) U.S. Cl.
CPC ............... *C07K 16/28* (2013.01); *C07K 7/06* (2013.01); *C07K 16/18* (2013.01); *C07K 2317/55* (2013.01); *C07K 2317/622* (2013.01); *C07K 2317/92* (2013.01); *C07K 2319/40* (2013.01); *C07K 2319/60* (2013.01); *G01N 33/531* (2013.01); *G01N 33/68* (2013.01); *C07K 1/22* (2013.01); *Y10S 435/961* (2013.01); *Y10S 435/975* (2013.01)
USPC .......... 530/413; 435/6.17; 435/7.1; 435/7.21; 435/69.3; 435/69.7; 435/70.21; 435/91.1; 435/331; 435/334; 435/320.1; 435/961; 435/975; 436/514; 436/518; 436/548; 530/326; 530/327; 530/387.9; 530/388.22; 530/391.1; 536/23.4; 536/23.5

(56) References Cited

FOREIGN PATENT DOCUMENTS

| WO | 98/06848 | * | 2/1998 |
|---|---|---|---|
| WO | 99/43809 | | 9/1999 |
| WO | 99/50415 | | 10/1999 |
| WO | 2005/121178 | | 12/2005 |

OTHER PUBLICATIONS

Eppinger et al., 2011. Genome sequences of the biotechnolgically important *Bacillus megaterium* strains QM B1551 and DSM319. J. Bacteriol. 193: 4199-4213, and reference sequence YP_003561896 attached thereto.*

Takahashi et al., 2001. Fas is required for clonal selection in germinal centers and the subsequent establishment of the memory B cell repertoire. Immunity 14: 181-192, and sequences AB043214 and AB043215 attached thereto.*

English Translation of the International Preliminary Report on Patentability (II), issued in connection with the corresponding PCT Application No. PCT/JP2008/073069. (Sep. 6, 2010).

Duellman, S.J., et al., "An epitope tag derived from human transcription factor IIB that reacts with a polyol-responsive monoclonal antibody", Protein Express. & Purif., (2004) vol. 35, pp. 147-155.

Thompson, N.E., et al., "Development of an epitope tag for the gentle purification of proteins by immunoaffinity chromatography: application to epitope-tagged green fluorescent protein", Anal. Biochem., (2003) vol. 323, pp. 171-179.

Nogi, T., et al., "Novel affinity tag system using structurally defined antibody-tag interaction: Application to single step protein purification", Protein Science, (Dec. 2008), vol. 17, No. 12, pp. 2120-2126.

T. Sangawa et al., "Development of Affinity-Tag System Using Anti-GPCR Monoclonal Antibody 20.1: I. Establishment of Antibody and Epitope Analysis", Protein Science Society of Japan Nenkai Program•Yoshishu, vol. $7^{th}$, p. 109, 2P-123, 2007 and English translation.

T. Nogi et al., "Development of Affinity-Tag System Using Anti-GPCR Monoclonal Antibody 20.1: II. X-Ray Crystallographic Analysis of Fab-Epitope Complex", Protein Science Society of Japan Nenkai Program•Yoshishu, vol. $7^{th}$, p. 109, 2P-124, 2007 and English translation.

S. Tabata et al., "Development of Affinity-Tag System Using Anti-GPCR Monoclonal Antibody 20.1: III. Screening of High-Affinity Peptide Sequence", Protein Science Society of Japan Nenkai Program•Yoshishu, vol. $7^{th}$, p. 110, 2P-125, 2007 and English translation.

W. Xu et al., "Cloning and Characterization of Human Protease-Activated Receptor 4", Proc. Natl. Acad. Sci. USA, vol. 95, pp. 6642-6646, Jun. 1998.

M. L. Kahn et al., "Protease-Activated Receptors 1 and 4 Mediate Activation of Human Platelets by Thrombin", The Journal of Clinical Investigation, vol. 103, No. 6, pp. 879-887, Mar. 1999.

L. Zhang et al., "Multiple Tandem Epitope Tagging for Enhanced Detection of Protein Expressed in Mammalian Cells", Molecular Biotechnology, vol. 19, pp. 313-321, 2001.

T. Sangawa et al., "A Murine Monoclonal Antibody that Binds N-Terminal Extracellular Segment of Human Protease-Activated Receptor-4", Hybridoma, vol. 27, No. 5, pp. 331-335, 2008.

S. Schneiker et al., GenBank Accession CAN97441, Mar. 26, 2008.

J. L. Lichty et al., "Comparison of Affinity Tags for Protein Purification", Protein Expression and Purification, vol. 41, pp. 98-105, 2005.

K. J. Morrow, "Advances in Epitope Tagging Strategies", Genetic Engineering & Biotechnology News, pp. 22-23, Apr. 1, 2007.

European Search Report mailed Nov. 26, 2012 in corresponding European Application No. 08871991.9.

Chinese Office Action, with partial English translation, issued Nov. 21, 2012 in corresponding Chinese Patent Application No. 2008801260988.

Nancy E. Thompson et al., "Identification of Polyol-Responsive Monoclonal Antibodies for Use in Immunoaffinity Chromatography", Section VI, Current Protocols in Molecular Biology, Immunology, 2001, pp. 6-14.

* cited by examiner

Fig.1

| | | |
|---|---|---|
| P4(20)-Fn | GGDDSTPSILPAPRGYPGQV─Fn9-10 | SEQ ID NO:2 |
| P4(N17)-Fn | GGDDSTPSILPAPRGY─Fn9-10 | SEQ ID NO:22 |
| P4(N14)-Fn | GGDDSTPSILPAPR─Fn9-10 | SEQ ID NO:23 |
| P4(C14)-Fn | PSILPAPRGYPGQV─Fn9-10 | SEQ ID NO:24 |
| P4(C6)-Fn | GYPGQV─Fn9-10 | SEQ ID NO:1 |
| Fn-P4(C8) | Fn9-10─PRGYPGQV | SEQ ID NO:25 |
| P4(G1A)-Fn | GGDDSTPSILPAPRAYPGQV─Fn9-10 | SEQ ID NO:26 |
| P4(Y2A)-Fn | GGDDSTPSILPAPRGAPGQV─Fn9-10 | SEQ ID NO:27 |
| P4(P3A)-Fn | GGDDSTPSILPAPRGYAGQV─Fn9-10 | SEQ ID NO:28 |
| P4(G4A)-Fn | GGDDSTPSILPAPRGYPAQV─Fn9-10 | SEQ ID NO:29 |
| P4(Q5A)-Fn | GGDDSTPSILPAPRGYPGAV─Fn9-10 | SEQ ID NO:30 |
| P4(V6A)-Fn | GGDDSTPSILPAPRGYPGQA─Fn9-10 | SEQ ID NO:31 |

Fig.2(a)

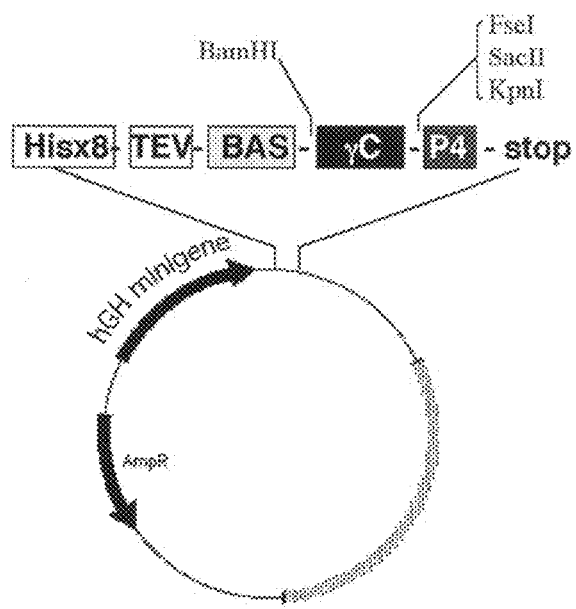

Fig.3

```
        2110      2120      2130      2140      2150      2160
     gacaaggtcgagacattcctgcgcatcgtgcagtgccgtctgtggagggcagctgtggc
      D  K  V  E  T  P  L  R  I  V  Q  C  R  S  V  E  G  S  C  G 2170      2180      2190      2200      2210      2220
     ttcagcggccaccaccaccaccaccaccacgactacgacatccctcctccgagaac
      F  S  G  H  H  H  H  H  H  H  H  D  Y  D  I  P  S  S  E  N 2230      2240      2250      2260      2270      2280
     ctgtacttccagGGATCTTCTTCCCTGAGACAGATCCTCGACAGCCAGAAGATGGAGTGG
      L  Y  F  Q  G  S  S  S  L  R  Q  I  L  D  S  Q  K  M  E  W 2290      2300      2310      2320      2330      2340
     CGCTCCAACGCAGGAGGCTCTTCCATGGGATCCatcactgggaaagattgtcaagacatt
      R  S  N  A  G  G  S  S  M  G  S  I  T  G  K  D  C  Q  D  I 2350      2360      2370      2380      2390      2400
     gccaataagggagctaaacagagcgggcttactttattaaacctctgaaagctaaccag
      A  N  K  G  A  K  Q  S  G  L  Y  F  I  K  P  L  K  A  N  Q 2410      2420      2430      2440      2450      2460
     caattcttagtctactgtgaaatcgatgggtctggaaatggatggactgtgtttcagaag
      Q  F  L  V  Y  C  E  I  D  G  S  G  N  G  W  T  V  F  Q  K 2470      2480      2490      2500      2510      2520
     agacttgatggcagtgtagatttcaagaaaaactggattcaatataaagaaggatttgga
      R  L  D  G  S  V  D  F  K  N  W  I  Q  Y  K  E  G  F  G 2530      2540      2550      2560      2570      2580
     catctgtctcctactggcacaacagaatttttggctgggaaatgagaagattcatttgata
      H  L  S  P  T  G  T  T  E  F  W  L  G  N  E  K  I  H  L  I 2590      2600      2610      2620      2630      2640
     agcacacagtctgccatcccatatgcattaagagtggaactggaagactggaatggcaga
      S  T  Q  S  A  I  P  Y  A  L  R  V  E  L  E  D  W  N  G  R 2650      2660      2670      2680      2690      2700
     accagtactgcagactatgccatgttcaaggtgggacctgaagctgacaagtaccgccta
      T  S  T  A  D  Y  A  M  F  K  V  G  P  E  A  D  K  Y  R  L 2710      2720      2730      2740      2750      2760
     acatatgcctacttcgctggtgggatgctggagatgcctttgatggctttgatttggc
      T  Y  A  Y  F  A  G  G  D  A  G  D  A  F  D  G  F  D  F  G 2770      2780      2790      2800      2810      2820
     gatgatcctagtgacaagttttcacatcccataatggcatgcagttcagtacctgggac
      D  D  P  S  D  K  F  F  T  S  N  G  M  Q  F  S  T  W  D 2830      2840      2850      2860      2870      2880
     aatgacaatgataagtttgaaggcaactgtgctgaacaggatggatctggttggtggatg
      N  D  N  D  K  F  E  G  N  C  A  E  Q  D  G  S  G  W  W 2890      2900      2910      2920      2930      2940
     aacaagtgtcacgctggccatctcaatggagtttattaccaaggtggcacttactcaaaa
      N  K  C  H  A  G  H  L  N  G  V  Y  Y  Q  G  G  T  Y  S  K 2950      2960      2970      2980      2990      3000
     gcatctactcctaatggttatgataatggcattatttgggccactggaaaaacccggtgg
      A  S  T  P  N  G  Y  D  N  G  I  I  W  A  T  W  K  T  R  W 3010      3020      3030      3040      3050      3060
     tattccatgaagaaaaccactatgaagataatcccattcaacagactcacaattggGCCG
      Y  S  M  K  K  T  T  M  K  I  I  P  F  N  R  L  T  I  G  P 3070      3080      3090      3100      3110      3120
     GCCCCGCGGGGTACCAGGACAATCtGAATTCtgatccagacatgataagatacattg
      A  P  R  G  Y  P  G  Q  V   SEQ ID NO:15 & 94
```

Fig.4(a)

(a)
```
        3010      3020      3030      3040      3050      3060
tattccatgaagaaaaccactatgaagataatcccattcaacagactcacaattggGCCG
 Y  S  M  K  K  T  T  M  K  I  I  P  F  N  R  L  T  I  G  P 3070      3080      3090      3100      3110      3120
GCCCCGCGGGGTACCCAGGACAAGTCggatatcctggtcaggttggctatccggccaa
 A  P  R  G  Y  P  G  Q  V  G  Y  P  G  Q  V  G  Y  P  G  Q 3130      3140      3150      3160      3170      3180
gtatGAATTCtgatccagacatgatgaagatacattgatgagttttggacaaaccacaacta
 V
```
SEQ ID NOs:32 & 33

Fig.4(b)

(b)
```
        3010      3020      3030      3040      3050      3060
tattccatgaagaaaaccactatgaagataatcccattcaacagactcacaattggGCCG
 Y  S  M  K  K  T  T  M  K  I  I  P  F  N  R  L  T  I  G  P 3070      3080      3090      3100      3110      3120
GCCCCGCGGGGTACCCAGGACAAGTCggatatcctggtcaggttggctatccggccaa
 A  P  R  G  Y  P  G  Q  V  G  Y  P  G  Q  V  G  Y  P  G  Q 3130      3140      3150      3160      3170      3180
gtaGGTTATCCTGGTCAAGTGGGTTACCCAGGGCAGGTCtGAATTCtgatccagacatga
 V  G  Y  P  G  Q  V  G  Y  P  G  Q  V
```
SEQ ID NOs:34 & 35

Fig.5

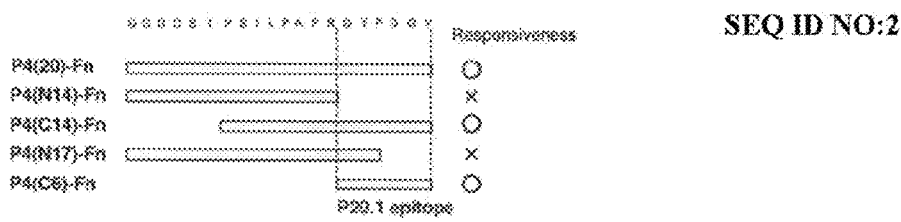

SEQ ID NO:2

Fig.6

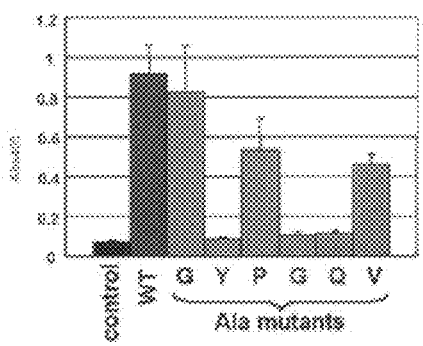

Fig.13

```
  1 CGTAGGCTCGAGAAGCTTGTCGACGAATTCAGATTACTAGTAGGAC ATGGGTTGGCTGTG  60
                                                  M  G  W  L  W

61 GAACTTCCCATTCCT GATGGCAGCAGCTCAAAGTATCCAAGCACAGATCCAGTTGGTGCA  120
        N  L  P  F  L  M  A  A  A  Q  S  I  Q  A  Q  I  Q  L  V  Q

121 GTCTGGACCTGAGGTGCAGAAGCCTGGAGAGACAGTCAGGATCTCCTGCAAGGCTTCTGG  180
     S  G  P  E  V  Q  K  P  G  E  T  V  R  I  S  C  K  A  S  G

181 GTATACCTTCACAACTGCTGGAATGCAGTGGGTGCAAAAGATGCCAGGAAAGAGTTTGAA  240
     Y  T  F  T  T  A  G  M  Q  W  V  Q  K  M  P  G  K  S  L  K
                     CDR-H1
241 GTGGATTGGCTGGATAAACACCCGCTCTGGAGTGCCAAAATATGCAGAAGACTTCAAGGG  300
     V  I  G  W  I  N  T  R  S  G  V  P  K  Y  A  E  D  F  K  G
                    CDR-H2
301 AGGTTTTGCCTTCTCTTTGGAAACGTCTGCCAGTATTGCATATTTACATATAAACAACCT  360
     R  F  A  F  S  L  E  T  S  A  S  I  A  Y  L  H  I  N  N  L

361 CAAAAATGAGGACACGGCTACCTATTTCTGTGCGAGAGAGGGGCCTGGATTTGTTTACTG  420
     K  N  E  D  T  A  T  Y  F  C  A  R  E  G  P  G  F  V  Y  W
                                          CDR-H3
421 GGGCCAAGGGACTCTGGTCACGGTCTCTGCAGGCAAAACGACACCCCCATCCGTCTATCC  480
     G  Q  G  T  L  V  T  V  S  A  A  K  T  T  P  P  S  V  Y  P

481 CCTGGCCCCTGGAAGT  496
     L  A  P  G  S                 SEQ ID NOs:3 & 4
```

Fig.14

```
  1  CGACTCACTATAGGGAAAGCTGGGTACCACGGCATGCTGCAGACGCGGTTACGTATCGGATC   60

61  CAGAATTCGTGATTGGGAATTCATGGCCTGGACTCCACTCTTACTCTCTCCTGGCTCT     120
                    M  A  W  T  P  L  L  L  S  L  L  A  L

121  CTGCTCAGGAGCCAGTTCCCAGACTGTTGTGACTCAGGAATCTGCACTCACGACATCACC   180
      C  S  X  A  S  S  Q  T  V  V  T  Q  E  S  A  L  T  T  S  P

181  TGGTGAAACAGTCACACTCACTTGTCGCTCAAGTACTGGGGTTGTTACAACTAGTAACTA   240
      G  E  T  V  T  L  T  C  R  S  S  T  G  V  V  T  T  S  N  Y
                                    CDR-L1

241  TGCCAACTGGGTCCAAGAAAAACCAGATCATTTATTCACTGGTCTAATAGTTGGTACCAA   300
      A  N  W  V  Q  E  K  P  D  H  L  F  T  G  L  I  V  G  T  N

301  GAACCGAGTTCCAGGTGTTGGTCCAGATTCTCAGGCTCCCTGATTGGAGACAAGGCTGC   360
      N  R  V  P  G  V  P  P  R  F  S  G  S  L  I  G  D  K  A  A
      CDR-L2

361  GCTCACGATCACAGGGGCACAGACTGAGGATGAGGCAATATATTTCTGTGCTCTATGGTA   420
      L  T  I  T  G  A  Q  T  E  D  E  A  I  Y  F  C  A  L  W  Y

421  CAGGAACGATTGGGTGTTCGGTGGAGGAACCAAACTGACTGTCCTAGGCCAGGGGAAGTC   480
      S  N  H  W  V  F  G  G  G  T  K  L  T  V  L  G  Q  P  K  S
      CDR-L3

481  TTCCCATCAGTCACCCTGTTTCCGCCCTCCTCTGAAGAGGTAAGCTTGGCAATCACGAA   540
      S  P  S  V  T  L  F  P  P  S  S  E  E  L  S  L  G  I  T  N

541  TTCTGGATCCGATACGTAAGGCGTCTGCAGCATGCGTGGTACCGAGCTTTCCCTATAGTG   600
      S  G  S  D  T  *

601  AGTCGTATTAGAGCTTGGGGTAATCATGGTCATAGCTGTTTNCGTGTGTGAAATNTTTAC   660

661  NAAA 664              SEQ ID NO:6 & 43
```

Fig.15

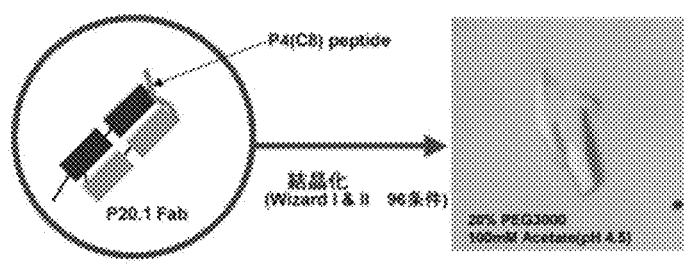

Fig. 17

```
  1 GGAAACAGCTATGAGGATGATTACGCCAAGCTTGCATGCAAATTCTATTTCAAGGAGACA   60

61 GTCATAATGAAATACCTATTGCCTACGGCAGCCGGTGGATTGTTATTACTCGCGGCGCAG  120
      M  K  Y  L  L  P  T  A  A  A  G  L  L  L  L  A  A  Q
        NcoI      PelB leader                          SfiI
121 GGGGCCATGGCCCAGATCCAGTTGGTGCAGTCTGGACCTGAGGTGCAGAAGCCTGGAGAG  180
     P  A  M  A  Q  I  Q  L  V  Q  S  G  P  E  V  Q  K  P  G  E
                    Heavy
181 AGAGTCAGGATCTGTGCAAGGCTTCTGGATATACCTTCACAACTGCTGGAATGCAGTGG   240
     R  V  R  I  S  C  K  A  S  G  Y  T  F  T  T  A  G  M  Q  W 241 GTGCAAAAGATGCCAGGAAAGAGTTTAAAGTGGATTGGCTGGATAAACAGCCGCTCTGGA  300
     V  Q  K  M  P  G  K  S  L  K  W  I  G  W  I  N  T  R  S  G 301 GTGCCAAAATATGCAGAAGACTTCAAGGGACGTTTTGCCTTGTCTTTGGAAACCTCTGCC  360
     V  P  K  Y  A  E  D  F  K  G  R  F  A  F  S  L  E  T  S  A 361 AGTATTGCATATTTACATATAAACAACCTCAAAAATGAGGACACGGCTACCTATTTCTGT  420
     S  I  A  Y  L  H  I  N  N  L  K  N  E  D  T  A  T  Y  F  C
                                                          XhoI
421 GGGAGAGAGGGGCCTGGATTTGTTTACTGGGGCCAAGGGACTCTGGTCACCGTCTCGAGC  480
     A  R  E  G  P  G  F  V  Y  W  G  Q  G  T  L  V  T  V  S  S
                                                        SalI
481 GGTGGAGGCGGTTCAGGCGGAGGTGGCAGCGGCGGTGGCGGGTCGACGCAGACTGTTGTG  540
     G  G  G  G  S  G  G  G  G  S  G  G  G  G  S  T  Q  T  V  V
                             Linker
541 ACTCAGGAATCTGCTCTCACCACATCACCTGGTGAAACAGTCACACTCACTTGTCGCTCA  600
     T  Q  E  S  A  L  T  T  S  P  G  E  T  V  T  L  T  C  R  S
                                Light
601 AGTACTGGGGCTGTTACAAGTAGTAACTATGCCAACTGGGTCCAAGAAAAACCAGATCAT  660
     S  T  G  A  V  T  S  S  N  Y  A  N  W  V  Q  E  K  P  D  H 661 TTATTCACTGGTCTAATAGTTGGTACGAACAACCGAGTTCGAGGTGTTCCTGGCAGATTC  720
     L  F  T  G  L  I  V  G  T  N  N  R  V  P  G  V  P  A  R  F 721 TGAGGCTCCCTGATTGAAGACAAGGCTGCCCTCACCATCACAGGGGCACAGACTGAGGAT  780
     S  G  S  L  I  E  D  K  A  A  L  T  I  T  G  A  Q  T  E  D 781 GAGGCAATATATTTCTGTGCTCTATGGTACAGCAACCATTGGGTGTTCGGTGGAGGAACC  840
     E  A  I  Y  F  C  A  L  W  Y  S  N  H  W  V  F  G  G  G  T
                                          NotI
841 AAACTGACTGTCCTAGGCGGCCGCCGGACATCATCATCACCATCACGGGGCGGCAGAACAA  900
     K  L  T  V  L  G  A  A  A  H  H  H  H  H  H  G  A  A  E  Q
                                HIS-tag
901 AAACTCATCTCAGAAGAGGATCTGAATGGGGCGGCATAAACT  942
     K  L  I  S  E  E  D  L  N  G  A  A  *  T           SEQ ID NOs:7 & 8
       Myc-tag
```

Fig. 18

Met - | Heavy chain | GGGGS Linker | Light chain | Core streptavidin | Myc | ×6His |

Regular P20.1 scFv fragment

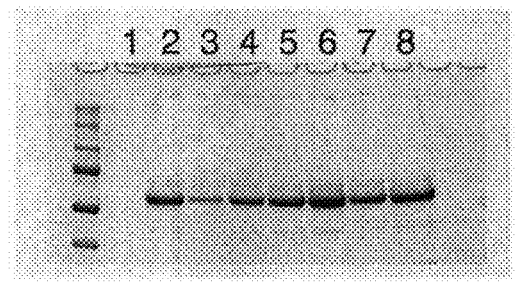

Fig.24

```
         910       920       930       940       950       960
TAAGCTTgatatcgaattccagttgggaaacATGctggacgcgagcggctgtagttgggc
                                 M  L  D  A  S  G  C  S  W  A 970       980       990      1000      1010      1020
gatgtggacgtgggcgctgttgcagctgctgctactagtggggccggaggctGCGGCCG
 M  N  T  W  A  L  L  Q  L  L  L  L  V  G  P  G  G   C  G  R 1030      1040      1050      1060      1070      1080
CGGGTACCCAGGACAAGTCGGATATCCTGGTCAGGTTGGCTATCCCGGCCAAGTAgagaa
 G  Y  P  G  Q  V  G  Y  P  G  Q  V  G  Y  P  G  Q  V  R  N 1090      1100      1110      1120      1130      1140
cctgtacttccagGGATCtggctactgtagccgtatcctgcgcgcccagggcacgcggc
 L  Y  F  Q  G  S  G  Y  C  S  R  I  L  R  A  Q  G  T  R  R 1150      1160      1170      1180      1190      1200
cgagggctacaccgagttcagcctccgcgtggagggcgacccggacttctacaagccggg
 E  G  Y  T  E  F  S  L  R  V  E  G  D  P  D  F  Y  K  P  G 1210      1220      1230      1240      1250      1260
aaccagctaccgcgtaacactttcagctgctcctcctcctacttcagaggattcacatt
 T  S  Y  R  V  T  L  S  A  A  P  P  S  Y  F  R  G  F  T  L 1270      1280      1290      1300      1310      1320
aattgccctcagagagaacagagagggtgataaggaagaagaccatgctggaccttcca
 I  A  L  R  E  N  R  E  G  D  K  E  E  D  H  A  G  T  F  Q 1330      1340      1350      1360      1370      1380
gatcatagacgaagaagaaactcagtttatgagcaattgccctgttgcagtcactgaaag
 I  I  D  E  E  E  T  Q  F  M  S  N  C  P  V  A  V  T  E  S 1390      1400      1410      1420      1430      1440
cactccacggaggaggacccggatccaggtgttttggatagcaccaccagcgggaacagg
 T  P  R  R  R  T  R  I  Q  V  F  W  I  A  P  P  A  G  T  G 1450      1460      1470      1480      1490      1500
ctgcgtgattctgaaggccagcatcgtacaaaaacgcattatttattttcaagatgaggg
 C  V  I  L  K  A  S  I  V  Q  K  R  I  I  Y  F  Q  D  E  G 1510      1520      1530      1540      1550      1560
ctctctgaccaagaaactttgtgaacaagattccTAATCTAGAgcgcgcacgcgtgcggc
 S  L  T  K  K  L  C  E  Q  D  S          SEQ ID NO:16 & 17
```

1: Marker
2: Supernatant from transient expression cell culture
3-4: Wash fractions
5-8: Eluted fractions ← F-spondin

SEQ ID NO:18

SEQUENCE LISTING

```
<160> NUMBER OF SEQ ID NOS: 96

<210> SEQ ID NO 1
<211> LENGTH: 6
<212> TYPE: PRT
<213> ORGANISM: Homo sapiens

<400> SEQUENCE: 1

Gly Tyr Pro Gly Gln Val
1               5

<210> SEQ ID NO 2
<211> LENGTH: 20
<212> TYPE: PRT
<213> ORGANISM: Homo sapiens

<400> SEQUENCE: 2

Gly Gly Asp Asp Ser Thr Pro Ser Ile Leu Pro Ala Pro Arg Gly Tyr
1               5                   10                  15

Pro Gly Gln Val
            20

<210> SEQ ID NO 3
<211> LENGTH: 496
<212> TYPE: DNA
<213> ORGANISM: Mouse
<220> FEATURE:
<221> NAME/KEY: CDS
<222> LOCATION: (47)..(496)

<400> SEQUENCE: 3
```

```
cctaggctcg agaagcttgt cgacgaattc agattactag tacgac atg ggt tgg          55
                                               Met Gly Trp
                                                 1 ctg tgg aac ttg cca ttc ctc atg gca gca gct caa agt atc caa gca        103
Leu Trp Asn Leu Pro Phe Leu Met Ala Ala Ala Gln Ser Ile Gln Ala
  5              10                  15 cag atc cag ttg gtg cag tct gga cct gag gtg cag aag cct gga gag        151
Gln Ile Gln Leu Val Gln Ser Gly Pro Glu Val Gln Lys Pro Gly Glu
 20                  25                  30                  35 aca gtc agg atc tcc tgc aag gct tct ggg tat acc ttc aca act gct        199
Thr Val Arg Ile Ser Cys Lys Ala Ser Gly Tyr Thr Phe Thr Thr Ala
                 40                  45                  50 gga atg cag tgg gtg caa aag atg cca gga aag agt ttg aag tgg att        247
Gly Met Gln Trp Val Gln Lys Met Pro Gly Lys Ser Leu Lys Trp Ile
             55                  60                  65 ggc tgg ata aac acc cgc tct gga gtg cca aaa tat gca gaa gac ttc        295
Gly Trp Ile Asn Thr Arg Ser Gly Val Pro Lys Tyr Ala Glu Asp Phe
         70                  75                  80 aag gga cgt ttt gcc ttc tct ttg gaa acc tct gcc agt att gca tat        343
Lys Gly Arg Phe Ala Phe Ser Leu Glu Thr Ser Ala Ser Ile Ala Tyr
 85                  90                  95 tta cat ata aac aac ctc aaa aat gag gac acg gct acc tat ttc tgt        391
Leu His Ile Asn Asn Leu Lys Asn Glu Asp Thr Ala Thr Tyr Phe Cys
100                 105                 110                 115 gcg aga gag ggg cct gga ttt gtt tac tgg ggc caa ggg act ctg gtc        439
Ala Arg Glu Gly Pro Gly Phe Val Tyr Trp Gly Gln Gly Thr Leu Val
                120                 125                 130 acc gtc tct gca gcc aaa acg aca ccc cca tcc gtc tat ccc ctg gcc        487
Thr Val Ser Ala Ala Lys Thr Thr Pro Pro Ser Val Tyr Pro Leu Ala
            135                 140                 145 cct gga agc                                                            496
Pro Gly Ser
        150

<210> SEQ ID NO 4
<211> LENGTH: 150
<212> TYPE: PRT
<213> ORGANISM: Mouse

<400> SEQUENCE: 4

Met Gly Trp Leu Trp Asn Leu Pro Phe Leu Met Ala Ala Ala Gln Ser
  1               5                  10                  15

Ile Gln Ala Gln Ile Gln Leu Val Gln Ser Gly Pro Glu Val Gln Lys
             20                  25                  30

Pro Gly Glu Thr Val Arg Ile Ser Cys Lys Ala Ser Gly Tyr Thr Phe
         35                  40                  45

Thr Thr Ala Gly Met Gln Trp Val Gln Lys Met Pro Gly Lys Ser Leu
     50                  55                  60

Lys Trp Ile Gly Trp Ile Asn Thr Arg Ser Gly Val Pro Lys Tyr Ala
 65                  70                  75                  80

Glu Asp Phe Lys Gly Arg Phe Ala Phe Ser Leu Glu Thr Ser Ala Ser
                 85                  90                  95

Ile Ala Tyr Leu His Ile Asn Asn Leu Lys Asn Glu Asp Thr Ala Thr
            100                 105                 110

Tyr Phe Cys Ala Arg Glu Gly Pro Gly Phe Val Tyr Trp Gly Gln Gly
        115                 120                 125

Thr Leu Val Thr Val Ser Ala Ala Lys Thr Thr Pro Pro Ser Val Tyr
    130                 135                 140
```

```
Pro Leu Ala Pro Gly Ser
145                 150

<210> SEQ ID NO 5
<211> LENGTH: 559
<212> TYPE: DNA
<213> ORGANISM: Mouse
<220> FEATURE:
<221> NAME/KEY: CDS
<222> LOCATION: (83)..(559)
<220> FEATURE:
<221> NAME/KEY: misc_feature
<222> LOCATION: (128)..(128)
<223> OTHER INFORMATION: n stands for unidentified base

<400> SEQUENCE: 5
cgactcacta tagggaaagc tcggtaccac gcatgctgca gacgcgttac gtatcggatc      60
cagaattcgt gattgggaat tc atg gcc tgg act cca ctc tta ctc tct ctc     112
                        Met Ala Trp Thr Pro Leu Leu Leu Ser Leu
                         1               5                  10 ctg gct ctc tgc tca nga gcc agt tcc cag act gtt gtg act cag gaa     160
Leu Ala Leu Cys Ser Xaa Ala Ser Ser Gln Thr Val Val Thr Gln Glu
             15                  20                  25 tct gca ctc acc aca tca cct ggt gaa aca gtc aca ctc act tgt cgc     208
Ser Ala Leu Thr Thr Ser Pro Gly Glu Thr Val Thr Leu Thr Cys Arg
         30                  35                  40 tca agt act ggg gtt gtt aca act agt aac tat gcc aac tgg gtc caa     256
Ser Ser Thr Gly Val Val Thr Thr Ser Asn Tyr Ala Asn Trp Val Gln
     45                  50                  55 gaa aaa cca gat cat tta ttc act ggt cta ata gtt ggt acc aac aac     304
Glu Lys Pro Asp His Leu Phe Thr Gly Leu Ile Val Gly Thr Asn Asn
 60                  65                  70 cga gtt cca ggt gtt cct ccc aga ttc tca ggc tcc ctg att gga gac     352
Arg Val Pro Gly Val Pro Pro Arg Phe Ser Gly Ser Leu Ile Gly Asp
 75                  80                  85                  90 aag gct gcc ctc acc atc aca ggg gca cag act gag gat gag gca ata     400
Lys Ala Ala Leu Thr Ile Thr Gly Ala Gln Thr Glu Asp Glu Ala Ile
                 95                 100                 105 tat ttc tgt gct cta tgg tac agc aac cat tgg gtg ttc ggt gga gga     448
Tyr Phe Cys Ala Leu Trp Tyr Ser Asn His Trp Val Phe Gly Gly Gly
             110                 115                 120 acc aaa ctg act gtc cta ggc cag ccc aag tct tcg cca tca gtc acc     496
Thr Lys Leu Thr Val Leu Gly Gln Pro Lys Ser Ser Pro Ser Val Thr
         125                 130                 135 ctg ttt ccg ccc tcc tct gaa gag cta agc ttg gga atc acg aat tct     544
Leu Phe Pro Pro Ser Ser Glu Glu Leu Ser Leu Gly Ile Thr Asn Ser
     140                 145                 150 gga tcc gat acg taa                                                  559
Gly Ser Asp Thr
155

<210> SEQ ID NO 6
<211> LENGTH: 158
<212> TYPE: PRT
<213> ORGANISM: Mouse
<220> FEATURE:
<221> NAME/KEY: misc_feature
<222> LOCATION: (16)..(16)
<223> OTHER INFORMATION: The 'Xaa' at location 16 stands for Arg, or
      Gly.

<400> SEQUENCE: 6

Met Ala Trp Thr Pro Leu Leu Leu Ser Leu Leu Ala Leu Cys Ser Xaa
```

```
              1               5                  10                 15
Ala Ser Ser Gln Thr Val Val Thr Gln Glu Ser Ala Leu Thr Thr Ser
                    20                  25                  30

Pro Gly Glu Thr Val Thr Leu Thr Cys Arg Ser Ser Thr Gly Val Val
                35                  40                  45

Thr Thr Ser Asn Tyr Ala Asn Trp Val Gln Glu Lys Pro Asp His Leu
        50                  55                  60

Phe Thr Gly Leu Ile Val Gly Thr Asn Asn Arg Val Pro Gly Val Pro
65                  70                  75                  80

Pro Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Gly Thr Lys Leu Thr Val Leu
                115                 120                 125

Gly Gln Pro Lys Ser Ser Pro Ser Val Thr Leu Phe Pro Pro Ser Ser
            130                 135                 140

Glu Glu Leu Ser Leu Gly Ile Thr Asn Ser Gly Ser Asp Thr
145                 150                 155

<210> SEQ ID NO 7
<211> LENGTH: 942
<212> TYPE: DNA
<213> ORGANISM: Artificial Sequence
<220> FEATURE:
<223> OTHER INFORMATION: Single chain Fab fragment of P20.1
<220> FEATURE:
<221> NAME/KEY: CDS
<222> LOCATION: (67)..(942)

<400> SEQUENCE: 7
ggaaacagct atgaccatga ttacgccaag cttgcatgca aattctattt caaggagaca    60 gtcata atg aaa tac cta ttg cct acg gca gcc gct gga ttg tta tta       108
       Met Lys Tyr Leu Leu Pro Thr Ala Ala Ala Gly Leu Leu Leu
       1               5                   10 ctc gcg gcc cag ccg gcc atg gcc cag atc cag ttg gtg cag tct gga      156
Leu Ala Ala Gln Pro Ala Met Ala Gln Ile Gln Leu Val Gln Ser Gly
15                  20                  25                  30 cct gag gtg cag aag cct gga gag aca gtc agg atc tcc tgc aag gct      204
Pro Glu Val Gln Lys Pro Gly Glu Thr Val Arg Ile Ser Cys Lys Ala
                35                  40                  45 tct ggg tat acc ttc aca act gct gga atg cag tgg gtg caa aag atg      252
Ser Gly Tyr Thr Phe Thr Thr Ala Gly Met Gln Trp Val Gln Lys Met
                50                  55                  60 cca gga aag agt ttg aag tgg att ggc tgg ata aac acc cgc tct gga      300
Pro Gly Lys Ser Leu Lys Trp Ile Gly Trp Ile Asn Thr Arg Ser Gly
65                  70                  75 gtg cca aaa tat gca gaa gac ttc aag gga cgt ttt gcc ttc tct ttg      348
Val Pro Lys Tyr Ala Glu Asp Phe Lys Gly Arg Phe Ala Phe Ser Leu
                80                  85                  90 gaa acc tct gcc agt att gca tat tta cat ata aac aac ctc aaa aat      396
Glu Thr Ser Ala Ser Ile Ala Tyr Leu His Ile Asn Asn Leu Lys Asn
95                  100                 105                 110 gag gac acg gct acc tat ttc tgt gcg aga gag ggg cct gga ttt gtt      444
Glu Asp Thr Ala Thr Tyr Phe Cys Ala Arg Glu Gly Pro Gly Phe Val
                115                 120                 125 tac tgg ggc caa ggg act ctg gtc acc gtc tcg agc ggt gga ggc ggt      492
Tyr Trp Gly Gln Gly Thr Leu Val Thr Val Ser Ser Gly Gly Gly Gly
            130                 135                 140
```

```
tca ggc gga ggt ggc agc ggt ggt ggc ggg tcg acg cag act gtt gtg     540
Ser Gly Gly Gly Gly Ser Gly Gly Gly Gly Ser Thr Gln Thr Val Val
            145                 150                 155 act cag gaa tct gct ctc acc aca tca cct ggt gaa aca gtc aca ctc     588
Thr Gln Glu Ser Ala Leu Thr Thr Ser Pro Gly Glu Thr Val Thr Leu
160                 165                 170 act tgt cgc tca agt act ggg gct gtt aca act agt aac tat gcc aac     636
Thr Cys Arg Ser Ser Thr Gly Ala Val Thr Thr Ser Asn Tyr Ala Asn
175                 180                 185                 190 tgg gtc caa gaa aaa cca gat cat tta ttc act ggt cta ata gtt ggt     684
Trp Val Gln Glu Lys Pro Asp His Leu Phe Thr Gly Leu Ile Val Gly
                195                 200                 205 acc aac aac cga gtt cca ggt gtt cct ccc aga ttc tca ggc tcc ctg     732
Thr Asn Asn Arg Val Pro Gly Val Pro Pro Arg Phe Ser Gly Ser Leu
            210                 215                 220 att gaa gac aag gct gcc ctc acc atc aca ggg gca cag act gag gat     780
Ile Glu Asp Lys Ala Ala Leu Thr Ile Thr Gly Ala Gln Thr Glu Asp
                225                 230                 235 gag gca ata tat ttc tgt gct cta tgg tac agc aac cat tgg gtg ttc     828
Glu Ala Ile Tyr Phe Cys Ala Leu Trp Tyr Ser Asn His Trp Val Phe
240                 245                 250 ggt gga gga acc aaa ctg act gtc cta ggc gcg gcc gca cat cat cat     876
Gly Gly Gly Thr Lys Leu Thr Val Leu Gly Ala Ala Ala His His His
255                 260                 265                 270 cac cat cac ggg gcc gca gaa caa aaa ctc atc tca gaa gag gat ctg     924
His His His Gly Ala Ala Glu Gln Lys Leu Ile Ser Glu Glu Asp Leu
                275                 280                 285 aat ggg gcc gca taa act                                             942
Asn Gly Ala Ala     Thr
            290

<210> SEQ ID NO 8
<211> LENGTH: 290
<212> TYPE: PRT
<213> ORGANISM: Artificial Sequence
<220> FEATURE:
<223> OTHER INFORMATION: Synthetic Construct

<400> SEQUENCE: 8

Met Lys Tyr Leu Leu Pro Thr Ala Ala Ala Gly Leu Leu Leu Leu Ala
1               5                   10                  15

Ala Gln Pro Ala Met Ala Gln Ile Gln Leu Val Gln Ser Gly Pro Glu
            20                  25                  30

Val Gln Lys Pro Gly Glu Thr Val Arg Ile Ser Cys Lys Ala Ser Gly
        35                  40                  45

Tyr Thr Phe Thr Thr Ala Gly Met Gln Trp Val Gln Lys Met Pro Gly
    50                  55                  60

Lys Ser Leu Lys Trp Ile Gly Trp Ile Asn Thr Arg Ser Gly Val Pro
65                  70                  75                  80

Lys Tyr Ala Glu Asp Phe Lys Gly Arg Phe Ala Phe Ser Leu Glu Thr
                85                  90                  95

Ser Ala Ser Ile Ala Tyr Leu His Ile Asn Asn Leu Lys Asn Glu Asp
            100                 105                 110

Thr Ala Thr Tyr Phe Cys Ala Arg Glu Gly Pro Gly Phe Val Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Thr Gln Thr Val Val Thr Gln
```

```
            145                 150                 155                 160
Glu Ser Ala Leu Thr Thr Ser Pro Gly Glu Thr Val Thr Leu Thr Cys
                165                 170                 175

Arg Ser Ser Thr Gly Ala Val Thr Thr Ser Asn Tyr Ala Asn Trp Val
            180                 185                 190

Gln Glu Lys Pro Asp His Leu Phe Thr Gly Leu Ile Val Gly Thr Asn
        195                 200                 205

Asn Arg Val Pro Gly Val Pro Pro Arg Phe Ser Gly Ser Leu Ile Glu
    210                 215                 220

Asp Lys Ala Ala Leu Thr Ile Thr Gly Ala Gln Thr Glu Asp Glu Ala
225                 230                 235                 240

Ile Tyr Phe Cys Ala Leu Trp Tyr Ser Asn His Trp Val Phe Gly Gly
                245                 250                 255

Gly Thr Lys Leu Thr Val Leu Gly Ala Ala Ala His His His His His
                260                 265                 270

His Gly Ala Ala Glu Gln Lys Leu Ile Ser Glu Glu Asp Leu Asn Gly
        275                 280                 285

Ala Ala
    290

<210> SEQ ID NO 9
<211> LENGTH: 18
<212> TYPE: DNA
<213> ORGANISM: Artificial Sequence
<220> FEATURE:
<223> OTHER INFORMATION: Synthetic construct; oligonucleotide coding tag
      peptide sequence (P4x1)
<220> FEATURE:
<221> NAME/KEY: CDS
<222> LOCATION: (1)..(18)

<400> SEQUENCE: 9 ggg tac cca gga caa gtc                                            18
Gly Tyr Pro Gly Gln Val
1               5

<210> SEQ ID NO 10

<400> SEQUENCE: 10

000

<210> SEQ ID NO 11
<211> LENGTH: 54
<212> TYPE: DNA
<213> ORGANISM: Artificial Sequence
<220> FEATURE:
<223> OTHER INFORMATION: Synthetic construct; oligonucleotide coding a
      tag peptide (P4x3)
<220> FEATURE:
<221> NAME/KEY: CDS
<222> LOCATION: (1)..(54)

<400> SEQUENCE: 11 ggg tac cca gga caa gtc gga tat cct ggt cag gtt ggc tat ccc ggc    48
Gly Tyr Pro Gly Gln Val Gly Tyr Pro Gly Gln Val Gly Tyr Pro Gly
1               5                   10                  15 caa gta                                                            54
Gln Val

<210> SEQ ID NO 12
<211> LENGTH: 18
<212> TYPE: PRT
```

<213> ORGANISM: Artificial Sequence
<220> FEATURE:
<223> OTHER INFORMATION: Synthetic Construct

<400> SEQUENCE: 12

```
Gly Tyr Pro Gly Gln Val Gly Tyr Pro Gly Gln Val Gly Tyr Pro Gly
1               5                   10                  15
Gln Val
```

<210> SEQ ID NO 13
<211> LENGTH: 90
<212> TYPE: DNA
<213> ORGANISM: Artificial Sequence
<220> FEATURE:
<223> OTHER INFORMATION: Synthetic construct; oligonucleotide coding a
      tag peptide (P4x5)
<220> FEATURE:
<221> NAME/KEY: CDS
<222> LOCATION: (1)..(90)

<400> SEQUENCE: 13

```
ggg tac cca gga caa gtc gga tat cct ggt cag gtt ggc tat ccc ggc     48
Gly Tyr Pro Gly Gln Val Gly Tyr Pro Gly Gln Val Gly Tyr Pro Gly
1               5                   10                  15 caa gta ggt tat cct ggt caa gtg ggt tac cca ggg cag gtc             90
Gln Val Gly Tyr Pro Gly Gln Val Gly Tyr Pro Gly Gln Val
            20                  25                  30
```

<210> SEQ ID NO 14
<211> LENGTH: 30
<212> TYPE: PRT
<213> ORGANISM: Artificial Sequence
<220> FEATURE:
<223> OTHER INFORMATION: Synthetic Construct

<400> SEQUENCE: 14

```
Gly Tyr Pro Gly Gln Val Gly Tyr Pro Gly Gln Val Gly Tyr Pro Gly
1               5                   10                  15
Gln Val Gly Tyr Pro Gly Gln Val Gly Tyr Pro Gly Gln Val
            20                  25                  30
```

<210> SEQ ID NO 15
<211> LENGTH: 1020
<212> TYPE: DNA
<213> ORGANISM: Artificial Sequence
<220> FEATURE:
<223> OTHER INFORMATION: Synthetic construct; part of a fusion protein
      (hGH-BAS-gamma C-P4) (DNA sequence of 2101-3210)

<400> SEQUENCE: 15

```
gacaaggtcg agacattcct gcgcatcgtg cagtgccgct ctgtggaggg cagctgtggc      60
ttcagcggcc accaccacca ccaccaccac cacgactacg acatcccctc ctccgagaac     120
ctgtacttcc agggatcttc tttccctgaga cagatcctcg acagccagaa gatggagtgg    180
cgctccaacg caggaggctc ttccatggga tccatcactg ggaaagattg tcaagacatt    240
gccaataagg gagctaaaca gagcgggctt tactttatta aacctctgaa agctaaccag    300
caattcttag tctactgtga aatcgatggg tctggaaatg gatggactgt gtttcagaag    360
agacttgatg gcagtgtaga tttcaagaaa actggattc aatataaaga aggatttgga    420
catctgtctc ctactggcac aacagaattt tggctgggaa atgagaagat tcatttgata    480
agcacacagt ctgccatccc atatgcatta agagtggaac tggaagactg gaatggcaga    540
accagtactg cagactatgc catgttcaag gtgggacctg aagctgacaa gtaccgccta    600
```

-continued

```
acatatgcct acttcgctgg tggggatgct ggagatgcct ttgatggctt tgattttggc      660
gatgatccta gtgacaagtt tttcacatcc cataatggca tgcagttcag tacctgggac      720
aatgacaatg ataagtttga aggcaactgt gctgaacagg atggatctgg ttggtggatg      780
aacaagtgtc acgctggcca tctcaatgga gtttattacc aaggtggcac ttactcaaaa      840
gcatctactc ctaatggtta tgataatggc attatttggg ccacttggaa aacccggtgg      900
tattccatga agaaaaccac tatgaagata atcccattca acagactcac aattgggccg      960
gccccgcggg ggtacccagg acaagtctga attctgatcc agacatgata agatacattg     1020
```

<210> SEQ ID NO 16
<211> LENGTH: 660
<212> TYPE: DNA
<213> ORGANISM: Artificial Sequence
<220> FEATURE:
<223> OTHER INFORMATION: Synthetic construct; part of recombinant
      F-spondin (DNA sequence of 901-1560)
<220> FEATURE:
<221> NAME/KEY: CDS
<222> LOCATION: (32)..(634)

<400> SEQUENCE: 16

```
taagcttgat atcgaattcc agttgggaaa c atg ctg gac gcg agc ggc tgt        52
                                   Met Leu Asp Ala Ser Gly Cys
                                     1               5 agt tgg gcg atg tgg acg tgg gcg ctg ttg cag ctg ctg cta cta gtg      100
Ser Trp Ala Met Trp Thr Trp Ala Leu Leu Gln Leu Leu Leu Leu Val
            10                  15                  20 ggg ccc gga ggc tgc ggc cgc ggg tac cca gga caa gtc gga tat cct      148
Gly Pro Gly Gly Cys Gly Arg Gly Tyr Pro Gly Gln Val Gly Tyr Pro
 25                  30                  35 ggt cag gtt ggc tat ccc ggc caa gta gag aac ctg tac ttc cag gga      196
Gly Gln Val Gly Tyr Pro Gly Gln Val Glu Asn Leu Tyr Phe Gln Gly
 40                  45                  50                  55 tct ggc tac tgt agc cgt atc ctc cgc gcc cag ggc acg cgg cgc gag      244
Ser Gly Tyr Cys Ser Arg Ile Leu Arg Ala Gln Gly Thr Arg Arg Glu
                 60                  65                  70 ggc tac acc gag ttc agc ctc cgc gtg gag ggc gac ccc gac ttc tac      292
Gly Tyr Thr Glu Phe Ser Leu Arg Val Glu Gly Asp Pro Asp Phe Tyr
             75                  80                  85 aag ccg gga acc agc tac cgc gta aca ctt tca gct gct cct ccc tcc      340
Lys Pro Gly Thr Ser Tyr Arg Val Thr Leu Ser Ala Ala Pro Pro Ser
         90                  95                 100 tac ttc aga gga ttc aca tta att gcc ctc aga gag aac aga gag ggt      388
Tyr Phe Arg Gly Phe Thr Leu Ile Ala Leu Arg Glu Asn Arg Glu Gly
     105                 110                 115 gat aag gaa gaa gac cat gct ggg acc ttc cag atc ata gac gaa gaa      436
Asp Lys Glu Glu Asp His Ala Gly Thr Phe Gln Ile Ile Asp Glu Glu
120                 125                 130                 135 gaa act cag ttt atg agc aat tgc cct gtt gca gtc act gaa agc act      484
Glu Thr Gln Phe Met Ser Asn Cys Pro Val Ala Val Thr Glu Ser Thr
                 140                 145                 150 cca cgg agg agg acc cgg atc cag gtg ttt tgg ata gca cca cca gcg      532
Pro Arg Arg Arg Thr Arg Ile Gln Val Phe Trp Ile Ala Pro Pro Ala
             155                 160                 165 gga aca ggc tgc gtg att ctg aag gcc agc atc gta caa aaa cgc att      580
Gly Thr Gly Cys Val Ile Leu Lys Ala Ser Ile Val Gln Lys Arg Ile
         170                 175                 180 att tat ttt caa gat gag ggc tct ctg acc aag aaa ctt tgt gaa caa      628
Ile Tyr Phe Gln Asp Glu Gly Ser Leu Thr Lys Lys Leu Cys Glu Gln
```

```
                     185                 190                 195
gat tcc taatctagag cgcgcacgcg tgcggc                              660
Asp Ser
200

<210> SEQ ID NO 17
<211> LENGTH: 201
<212> TYPE: PRT
<213> ORGANISM: Artificial Sequence
<220> FEATURE:
<223> OTHER INFORMATION: Synthetic Construct

<400> SEQUENCE: 17

Met Leu Asp Ala Ser Gly Cys Ser Trp Ala Met Trp Thr Trp Ala Leu
1               5                   10                  15

Leu Gln Leu Leu Leu Val Gly Pro Gly Cys Gly Arg Gly Tyr
            20                  25                  30

Pro Gly Gln Val Gly Tyr Pro Gly Gln Val Gly Tyr Pro Gly Gln Val
        35                  40                  45

Glu Asn Leu Tyr Phe Gln Gly Ser Gly Tyr Cys Ser Arg Ile Leu Arg
    50                  55                  60

Ala Gln Gly Thr Arg Arg Glu Gly Tyr Thr Glu Phe Ser Leu Arg Val
65                  70                  75                  80

Glu Gly Asp Pro Asp Phe Tyr Lys Pro Gly Thr Ser Tyr Arg Val Thr
                85                  90                  95

Leu Ser Ala Ala Pro Pro Ser Tyr Phe Arg Gly Phe Thr Leu Ile Ala
            100                 105                 110

Leu Arg Glu Asn Arg Glu Gly Asp Lys Glu Glu Asp His Ala Gly Thr
        115                 120                 125

Phe Gln Ile Ile Asp Glu Glu Glu Thr Gln Phe Met Ser Asn Cys Pro
    130                 135                 140

Val Ala Val Thr Glu Ser Thr Pro Arg Arg Arg Thr Arg Ile Gln Val
145                 150                 155                 160

Phe Trp Ile Ala Pro Pro Ala Gly Thr Gly Cys Val Ile Leu Lys Ala
                165                 170                 175

Ser Ile Val Gln Lys Arg Ile Ile Tyr Phe Gln Asp Glu Gly Ser Leu
            180                 185                 190

Thr Lys Lys Leu Cys Glu Gln Asp Ser
        195                 200

<210> SEQ ID NO 18
<211> LENGTH: 4
<212> TYPE: PRT
<213> ORGANISM: Homo sapiens

<400> SEQUENCE: 18

Tyr Pro Gly Gln
1

<210> SEQ ID NO 19
<211> LENGTH: 8
<212> TYPE: PRT
<213> ORGANISM: Artificial Sequence
<220> FEATURE:
<223> OTHER INFORMATION: Synthetic construct; FLAG tag

<400> SEQUENCE: 19

Asp Tyr Lys Asp Asp Asp Val
1               5
```

```
<210> SEQ ID NO 20
<211> LENGTH: 8
<212> TYPE: PRT
<213> ORGANISM: Homo sapiens

<400> SEQUENCE: 20

Pro Arg Gly Tyr Pro Gly Gln Val
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic construct; tag peptide
<220> FEATURE:
<221> NAME/KEY: MISC_FEATURE
<222> LOCATION: (1)..(1)
<223> OTHER INFORMATION: Xaa may be any amino acid
<220> FEATURE:
<221> NAME/KEY: MISC_FEATURE
<222> LOCATION: (3)..(3)
<223> OTHER INFORMATION: may include a small side chain, such as S, V,
      C, A, T, E, G, and D
<220> FEATURE:
<221> NAME/KEY: MISC_FEATURE
<222> LOCATION: (6)..(6)
<223> OTHER INFORMATION: Xaa may be any hydrophobic amino acid

<400> SEQUENCE: 21

Xaa Tyr Pro Gly Gln Xaa
1               5

<210> SEQ ID NO 22
<211> LENGTH: 16
<212> TYPE: PRT
<213> ORGANISM: Homo sapiens

<400> SEQUENCE: 22

Gly Gly Asp Asp Ser Thr Pro Ser Ile Leu Pro Ala Pro Arg Gly Tyr
1               5                   10                  15

<210> SEQ ID NO 23
<211> LENGTH: 14
<212> TYPE: PRT
<213> ORGANISM: Homo sapiens

<400> SEQUENCE: 23

Gly Gly Asp Asp Ser Thr Pro Ser Ile Leu Pro Ala Pro Arg
1               5                   10

<210> SEQ ID NO 24
<211> LENGTH: 14
<212> TYPE: PRT
<213> ORGANISM: Homo sapiens

<400> SEQUENCE: 24

Pro Ser Ile Leu Pro Ala Pro Arg Gly Tyr Pro Gly Gln Val
1               5                   10

<210> SEQ ID NO 25
<211> LENGTH: 8
<212> TYPE: PRT
<213> ORGANISM: Homo sapiens

<400> SEQUENCE: 25

Pro Arg Gly Tyr Pro Gly Gln Val
```

-continued

```
<210> SEQ ID NO 26
<211> LENGTH: 20
<212> TYPE: PRT
<213> ORGANISM: Homo sapiens

<400> SEQUENCE: 26

Gly Gly Asp Asp Ser Thr Pro Ser Ile Leu Pro Ala Pro Arg Ala Tyr
1               5                   10                  15

Pro Gly Gln Val
        20

<210> SEQ ID NO 27
<211> LENGTH: 20
<212> TYPE: PRT
<213> ORGANISM: Homo sapiens

<400> SEQUENCE: 27

Gly Gly Asp Asp Ser Thr Pro Ser Ile Leu Pro Ala Pro Arg Gly Ala
1               5                   10                  15

Pro Gly Gln Val
        20

<210> SEQ ID NO 28
<211> LENGTH: 20
<212> TYPE: PRT
<213> ORGANISM: Homo sapiens

<400> SEQUENCE: 28

Gly Gly Asp Asp Ser Thr Pro Ser Ile Leu Pro Ala Pro Arg Gly Tyr
1               5                   10                  15

Ala Gly Gln Val
        20

<210> SEQ ID NO 29
<211> LENGTH: 20
<212> TYPE: PRT
<213> ORGANISM: Homo sapiens

<400> SEQUENCE: 29

Gly Gly Asp Asp Ser Thr Pro Ser Ile Leu Pro Ala Pro Arg Gly Tyr
1               5                   10                  15

Pro Ala Gln Val
        20

<210> SEQ ID NO 30
<211> LENGTH: 20
<212> TYPE: PRT
<213> ORGANISM: Homo sapiens

<400> SEQUENCE: 30

Gly Gly Asp Asp Ser Thr Pro Ser Ile Leu Pro Ala Pro Arg Gly Tyr
1               5                   10                  15

Pro Gly Ala Val
        20

<210> SEQ ID NO 31
<211> LENGTH: 20
<212> TYPE: PRT
<213> ORGANISM: Homo sapiens

<400> SEQUENCE: 31
```

```
Gly Gly Asp Asp Ser Thr Pro Ser Ile Leu Pro Ala Pro Arg Gly Tyr
1               5                   10                  15

Pro Gly Gln Ala
            20

<210> SEQ ID NO 32
<211> LENGTH: 180
<212> TYPE: DNA
<213> ORGANISM: Artificial Sequence
<220> FEATURE:
<223> OTHER INFORMATION: Synthetic construct; tag peptide fusion protein
<220> FEATURE:
<221> NAME/KEY: CDS
<222> LOCATION: (1)..(123)

<400> SEQUENCE: 32 tat tcc atg aag aaa acc act atg aag ata atc cca ttc aac aga ctc        48
Tyr Ser Met Lys Lys Thr Thr Met Lys Ile Ile Pro Phe Asn Arg Leu
1               5                   10                  15 aca att ggg ccg gcc ccg cgg ggg tac cca gga caa gtc gga tat cct        96
Thr Ile Gly Pro Ala Pro Arg Gly Tyr Pro Gly Gln Val Gly Tyr Pro
            20                  25                  30 ggt cag gtt ggc tat ccc ggc caa gta tgaattctga tccagacatg           143
Gly Gln Val Gly Tyr Pro Gly Gln Val
        35                  40 ataagataca ttgatgagtt tggacaaacc acaacta                            180

<210> SEQ ID NO 33
<211> LENGTH: 41
<212> TYPE: PRT
<213> ORGANISM: Artificial Sequence
<220> FEATURE:
<223> OTHER INFORMATION: Synthetic Construct

<400> SEQUENCE: 33

Tyr Ser Met Lys Lys Thr Thr Met Lys Ile Ile Pro Phe Asn Arg Leu
1               5                   10                  15

Thr Ile Gly Pro Ala Pro Arg Gly Tyr Pro Gly Gln Val Gly Tyr Pro
            20                  25                  30

Gly Gln Val Gly Tyr Pro Gly Gln Val
        35                  40

<210> SEQ ID NO 34
<211> LENGTH: 180
<212> TYPE: DNA
<213> ORGANISM: Artificial Sequence
<220> FEATURE:
<223> OTHER INFORMATION: Synthetic construct: tag peptide fusion protein
<220> FEATURE:
<221> NAME/KEY: CDS
<222> LOCATION: (1)..(159)

<400> SEQUENCE: 34 tat tcc atg aag aaa acc act atg aag ata atc cca ttc aac aga ctc        48
Tyr Ser Met Lys Lys Thr Thr Met Lys Ile Ile Pro Phe Asn Arg Leu
1               5                   10                  15 aca att ggg ccg gcc ccg cgg ggg tac cca gga caa gtc gga tat cct        96
Thr Ile Gly Pro Ala Pro Arg Gly Tyr Pro Gly Gln Val Gly Tyr Pro
            20                  25                  30 ggt cag gtt ggc tat ccc ggc caa gta ggt tat cct ggt caa gtg ggt       144
Gly Gln Val Gly Tyr Pro Gly Gln Val Gly Tyr Pro Gly Gln Val Gly
        35                  40                  45 tac cca ggg cag gtc tgaattctga tccagacatg a                         180
```

Tyr Pro Gly Gln Val
            50

<210> SEQ ID NO 35
<211> LENGTH: 53
<212> TYPE: PRT
<213> ORGANISM: Artificial Sequence
<220> FEATURE:
<223> OTHER INFORMATION: Synthetic Construct

<400> SEQUENCE: 35

Tyr Ser Met Lys Lys Thr Thr Met Lys Ile Ile Pro Phe Asn Arg Leu
1               5                   10                  15

Thr Ile Gly Pro Ala Pro Arg Gly Tyr Pro Gly Gln Val Gly Tyr Pro
            20                  25                  30

Gly Gln Val Gly Tyr Pro Gly Gln Val Gly Tyr Pro Gly Gln Val Gly
        35                  40                  45

Tyr Pro Gly Gln Val
            50

<210> SEQ ID NO 36
<211> LENGTH: 47
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 36
catgccatgg ccnnktacnn kcaannknnk ggaggctcga gcgtaag          47

<210> SEQ ID NO 37
<211> LENGTH: 12
<212> TYPE: PRT
<213> ORGANISM: Artificial Sequence
<220> FEATURE:
<223> OTHER INFORMATION: Synthetic construct; tag peptide

<400> SEQUENCE: 37

Tyr Pro Gly Gln Tyr Pro Gly Gln Tyr Pro Gly Gln
1               5                   10

<210> SEQ ID NO 38
<211> LENGTH: 16
<212> TYPE: PRT
<213> ORGANISM: Artificial Sequence
<220> FEATURE:
<223> OTHER INFORMATION: Synthetic construct; tag peptide

<400> SEQUENCE: 38

Tyr Pro Gly Gln Tyr Pro Gly Gln Tyr Pro Gly Gln Tyr Pro Gly Gln
1               5                   10                  15

```
<210> SEQ ID NO 39
<211> LENGTH: 20
<212> TYPE: PRT
<213> ORGANISM: Artificial Sequence
<220> FEATURE:
<223> OTHER INFORMATION: Synthetic construct; tag peptide

<400> SEQUENCE: 39

Tyr Pro Gly Gln Tyr Pro Gly Gln Tyr Pro Gly Gln Tyr Pro Gly Gln
1               5                   10                  15

Tyr Pro Gly Gln
            20

<210> SEQ ID NO 40
<211> LENGTH: 13
<212> TYPE: PRT
<213> ORGANISM: Artificial Sequence
<220> FEATURE:
<223> OTHER INFORMATION: Synthetic construct; tag peptide

<400> SEQUENCE: 40

Tyr Pro Gly Gln Tyr Pro Gly Gln Tyr Pro Gly Gln Val
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Synthetic construct; tag peptide

<400> SEQUENCE: 41

Tyr Pro Gly Gln Tyr Pro Gly Gln Tyr Pro Gly Gln Tyr Pro Gly Gln
1               5                   10                  15

Val

<210> SEQ ID NO 42
<211> LENGTH: 21
<212> TYPE: PRT
<213> ORGANISM: Artificial Sequence
<220> FEATURE:
<223> OTHER INFORMATION: Synthetic construct; tag peptide

<400> SEQUENCE: 42

Tyr Pro Gly Gln Tyr Pro Gly Gln Tyr Pro Gly Gln Tyr Pro Gly Gln
1               5                   10                  15

Tyr Pro Gly Gln Val
            20

<210> SEQ ID NO 43
<211> LENGTH: 664
<212> TYPE: DNA
<213> ORGANISM: Mouse
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
```

<222> LOCATION: (661)..(661)
<223> OTHER INFORMATION: n is a, c, g, or t

<400> SEQUENCE: 43

```
cgactcacta tagggaaagc tcggtaccac gcatgctgca gacgcgttac gtatcggatc    60
cagaattcgt gattgggaat tcatggcctg gactccactc ttactctctc tcctggctct   120
ctgctcanga gccagttccc agactgttgt gactcaggaa tctgcactca ccacatcacc   180
tggtgaaaca gtcacactca cttgtcgctc aagtactggg gttgttacaa ctagtaacta   240
tgccaactgg gtccaagaaa accagatca tttattcact ggtctaatag ttggtaccaa    300
caaccgagtt ccaggtgttc ctcccagatt ctcaggctcc ctgattggag acaaggctgc   360
cctcaccatc acaggggcac agactgagga tgaggcaata tatttctgtg ctctatggta   420
cagcaaccat gggtgttcg gtggaggaac caaactgact gtcctaggcc agcccaagtc    480
ttcgccatca gtcaccctgt tccgccctc ctctgaagag ctaagcttgg gaatcacgaa    540
ttctggatcc gatacgtaac gcgtctgcag catgcgtggt accgagcttt ccctatagtg   600
agtcgtatta gagcttggcg taatcatggt catagctgtt tncctgtgtg aaatntttac   660
naaa                                                                664
```

<210> SEQ ID NO 44
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 44

Asp Tyr Pro Gly Gln Val Cys
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 45

Ile Tyr Pro Gly Gln Trp Gly
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 46

Gln Tyr Ser Gly Gln Trp Pro
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

```
<400> SEQUENCE: 47

Leu Tyr Val Gly Gln Val Gly
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 48

Ser Tyr Ser Gly Gln Val His
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 49

Tyr Tyr Ser Gly Gln Val Gln
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 50

Ser Tyr Pro Gly Gln Met Asn
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 51

Arg Tyr Ser Gly Gln Val Gly
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 52

Val Tyr Pro Gly Gln Leu Asn
1               5

<210> SEQ ID NO 53
<211> LENGTH: 7
```

<212> TYPE: PRT
<213> ORGANISM: Artificial Sequence
<220> FEATURE:
<223> OTHER INFORMATION: Synthetic construct: peptide recognition
sequence for P20.1 antibody

<400> SEQUENCE: 53

Arg Tyr Pro Gly Gln Thr Gly
1 5

<210> SEQ ID NO 54
<211> LENGTH: 7
<212> TYPE: PRT
<213> ORGANISM: Artificial Sequence
<220> FEATURE:
<223> OTHER INFORMATION: Synthetic construct: peptide recognition
sequence for P20.1 antibody

<400> SEQUENCE: 54

Trp Tyr Pro Gly Gln Leu Glu
1 5

<210> SEQ ID NO 55
<211> LENGTH: 7
<212> TYPE: PRT
<213> ORGANISM: Artificial Sequence
<220> FEATURE:
<223> OTHER INFORMATION: Synthetic construct: peptide recognition
sequence for P20.1 antibody

<400> SEQUENCE: 55

Gly Tyr Cys Val Gln Leu Gln
1 5

<210> SEQ ID NO 56
<211> LENGTH: 7
<212> TYPE: PRT
<213> ORGANISM: Artificial Sequence
<220> FEATURE:
<223> OTHER INFORMATION: Synthetic construct: peptide recognition
sequence for P20.1 antibody

<400> SEQUENCE: 56

Thr Tyr Pro Gly Gln Leu Glu
1 5

<210> SEQ ID NO 57
<211> LENGTH: 7
<212> TYPE: PRT
<213> ORGANISM: Artificial Sequence
<220> FEATURE:
<223> OTHER INFORMATION: Synthetic construct: peptide recognition
sequence for P20.1 antibody

<400> SEQUENCE: 57

Ser Tyr Gln Gly Gln Trp Thr
1 5

<210> SEQ ID NO 58
<211> LENGTH: 7
<212> TYPE: PRT
<213> ORGANISM: Artificial Sequence
<220> FEATURE:
<223> OTHER INFORMATION: Synthetic construct: peptide recognition
sequence for P20.1 antibody

<400> SEQUENCE: 58

Trp Tyr Pro Gly Gln Leu Glu

```
1               5
```

<210> SEQ ID NO 59
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 59

```
Arg Tyr Val Gly Gln Ile Pro
1               5
```

<210> SEQ ID NO 60
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 60

```
Thr Tyr Pro Gly Gln Val Arg
1               5
```

<210> SEQ ID NO 61
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 61

```
Leu Tyr Pro Gly Gln Val Val
1               5
```

<210> SEQ ID NO 62
<211> LENGTH: 7
<212> TYPE: PRT
<213> ORGANISM: Artificial Sequence
<220> FEATURE:
<223> OTHER INFORMATION: Synthetic construct: peptide recognition sequence for P20.1 antibody

<400> SEQUENCE: 62

Asp Tyr Gln Gly Gln Val Pro
1 5

<210> SEQ ID NO 63
<211> LENGTH: 7
<212> TYPE: PRT
<213> ORGANISM: Artificial Sequence
<220> FEATURE:
<223> OTHER INFORMATION: Synthetic construct: peptide recognition sequence for P20.1 antibody

<400> SEQUENCE: 63

Ser Tyr Pro Gly Gln Val Gly
1 5

<210> SEQ ID NO 64
<211> LENGTH: 7
<212> TYPE: PRT
<213> ORGANISM: Artificial Sequence
<220> FEATURE:
<223> OTHER INFORMATION: Synthetic construct: peptide recognition -continued sequence for P20.1 antibody

<400> SEQUENCE: 64

Val Tyr Asp Gly Gln Ile Ser
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 65

Leu Tyr Pro Gly Gln Ala Val
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 66

Arg Tyr Pro Gly Gln Val Ala
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 67

Arg Tyr Ala Gly Gln Val Pro
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 68

Thr Tyr Pro Gly Gln Glu Glu
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 69

Leu Tyr Ala Gly Gln Val Pro
1               5

<210> SEQ ID NO 70

```
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 70

Arg Tyr Pro Gly Gln Val Asp
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 71

Leu Tyr Glu Ala Gln Gln Met
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 72

Trp Tyr Thr Gly Gln Ala Pro
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 73

Asp Tyr Gln Ser Gln Pro Leu
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 74

Ser Tyr Ala Gly Gln Ile Gly
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 75
```

Met Tyr Ala Gly Gln Tyr Val
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 76

Arg Tyr Pro Gly Gln Leu Leu
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 77

Gly Tyr Ser Gly Gln Val Gly
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 78

Ser Tyr Pro Gly Gln Val Met
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 79

Met Tyr Ser Gly Gln Val Pro
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 80

Phe Tyr Gly Glu Gln Ser Met
1               5

<210> SEQ ID NO 81
<211> LENGTH: 7
<212> TYPE: PRT
<213> ORGANISM: Artificial Sequence
<220> FEATURE:

<223> OTHER INFORMATION: Synthetic construct: peptide recognition
      sequence for P20.1 antibody

<400> SEQUENCE: 81

Leu Tyr Pro Gly Gln Ala Val
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 82

Phe Tyr Glu Gln Gln Asn Arg
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 83

Gln Tyr Pro Gly Gln Val Ile
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 84

His Tyr Pro Gly Gln Ala Trp
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 85

Arg Tyr Pro Gly Gln Met Ser
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 86

Asp Tyr Asp Gly Gln Phe Pro
1               5

```
<210> SEQ ID NO 87
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 87

Trp Tyr Pro Gly Gln Leu Glu
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 88

Met Tyr Thr Gly Gln Thr Val
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 89

Lys Tyr Gly Gly Gln Val Pro
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 90

Val Tyr Pro Gly Gln Tyr Arg
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 91

Ala Tyr Gln Gly Gln Val Pro
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 92
```

Gly Tyr Pro Gly Gln Trp Ser
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic construct: peptide recognition
      sequence for P20.1 antibody

<400> SEQUENCE: 93

Trp Tyr Pro Gly Gln Leu Glu
1               5

<210> SEQ ID NO 94
<211> LENGTH: 329
<212> TYPE: PRT
<213> ORGANISM: Artificial Sequence
<220> FEATURE:
<223> OTHER INFORMATION: Synthetic construct; part of a fusion protein
      (hGH-BAS-gamma C-P4)

<400> SEQUENCE: 94

Asp Lys Val Glu Thr Phe Leu Arg Ile Val Gln Cys Arg Ser Val Glu
1               5                   10                  15

Gly Ser Cys Gly Phe Ser Gly His His His His His His His Asp
            20                  25                  30

Tyr Asp Ile Pro Ser Ser Glu Asn Leu Tyr Phe Gln Gly Ser Ser Ser
        35                  40                  45

Leu Arg Gln Ile Leu Asp Ser Gln Lys Met Glu Trp Arg Ser Asn Ala
    50                  55                  60

Gly Gly Ser Ser Met Gly Ser Ile Thr Gly Lys Asp Cys Gln Asp Ile
65                  70                  75                  80

Ala Asn Lys Gly Ala Lys Gln Ser Gly Leu Tyr Phe Ile Lys Pro Leu
                85                  90                  95

Lys Ala Asn Gln Gln Phe Leu Val Tyr Cys Glu Ile Asp Gly Ser Gly
            100                 105                 110

Asn Gly Trp Thr Val Phe Gln Lys Arg Leu Asp Gly Ser Val Asp Phe
        115                 120                 125

Lys Lys Asn Trp Ile Gln Tyr Lys Glu Gly Phe Gly His Leu Ser Pro
130                 135                 140

Thr Gly Thr Thr Glu Phe Trp Leu Gly Asn Glu Lys Ile His Leu Ile
145                 150                 155                 160

Ser Thr Gln Ser Ala Ile Pro Tyr Ala Leu Arg Val Glu Leu Glu Asp
                165                 170                 175

Trp Asn Gly Arg Thr Ser Thr Ala Asp Tyr Ala Met Phe Lys Val Gly
            180                 185                 190

Pro Glu Ala Asp Lys Tyr Arg Leu Thr Tyr Ala Tyr Phe Ala Gly Gly
        195                 200                 205

Asp Ala Gly Asp Ala Phe Asp Gly Phe Asp Phe Gly Asp Asp Pro Ser
    210                 215                 220

Asp Lys Phe Phe Thr Ser His Asn Gly Met Gln Phe Ser Thr Trp Asp
225                 230                 235                 240

Asn Asp Asn Asp Lys Phe Glu Gly Asn Cys Ala Glu Gln Asp Gly Ser
                245                 250                 255

Gly Trp Trp Met Asn Lys Cys His Ala Gly His Leu Asn Gly Val Tyr
            260                 265                 270

```
Tyr Gln Gly Gly Thr Tyr Ser Lys Ala Ser Thr Pro Asn Gly Tyr Asp
            275                 280                 285

Asn Gly Ile Ile Trp Ala Thr Trp Lys Thr Arg Trp Tyr Ser Met Lys
        290                 295                 300

Lys Thr Thr Met Lys Ile Ile Pro Phe Asn Arg Leu Thr Ile Gly Pro
305                 310                 315                 320

Ala Pro Arg Gly Tyr Pro Gly Gln Val
                325

<210> SEQ ID NO 95
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is any amino acid residue
<220> FEATURE:
<221> NAME/KEY: MISC_FEATURE
<222> LOCATION: (3)..(3)
<223> OTHER INFORMATION: Xaa is any amino acid residue
<220> FEATURE:
<221> NAME/KEY: MISC_FEATURE
<222> LOCATION: (6)..(6)
<223> OTHER INFORMATION: Xaa is any amino acid residue

<400> SEQUENCE: 95

Xaa Tyr Xaa Gly Gln Xaa
1               5

<210> SEQ ID NO 96
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is any amino acid

<400> SEQUENCE: 96

Tyr Xaa Gly Gln
1
```

TAG PEPTIDE AND USE THEREOF

This application is a U.S. national stage of International Application No. PCT/W2008/073069 filed Dec. 18, 2008.

The Sequence Listing filed Dec. 20, 2012, having the file name of 2010-0937A_ST25, created on Dec. 19, 2012, having a size of 34 KB, is herein incorporated by reference in its entirety.

TECHNICAL FIELD

The present invention relates to a tag peptide and use thereof, and in particular relates to a tag peptide that can be applied to protein purification, detection or quantification, a tag peptide fusion protein having the tag peptide linked thereto, a polynucleotide encoding the tag peptide, a recombinant vector containing the polynucleotide, an antibody against the tag peptide, a protein purification, detection or quantification method using the antibody, and a kit using the same.

BACKGROUND ART

In the life science field, preparation of recombinant proteins is performed as a part of basic research, applied research and product development. However, there are a limited number of techniques for isolating and purifying the proteins in high purity.

Affinity chromatography is one of the most powerful means for protein purification. As an isolation and purification method for proteins using affinity chromatography, a method involving attaching a histidine-containing peptide of 6 to 10 residues (histidine tag) to the N or C terminus of proteins and using the interaction of the histidine tag and a metal such as nickel is known. A method using the interaction of a tag peptide (peptide tag) and an antibody thereagainst is also known (for example, nonpatent literatures 1 and 2).

However, in the former method using the histidine tag, because of low specificity between nickel and the histidine tag, proteins other than objective proteins (histidine tagged proteins), and even compounds other than proteins adsorb onto the column. Therefore, this method has a problem in that highly purified proteins cannot be obtained in a single purification step.

As a detection and purification system for proteins using the interaction of a tag peptide and an antibody thereagainst like the latter method, a FLAG (registered trademark) system commercially available from Sigma is used extensively. This technique, in which a FLAG peptide and an antibody thereagainst (antibodies M1 and M2, etc.) are used, is currently considered the most excellent in specificity. However, the FLAG (registered trademark) system is so expensive that it may be limitedly used in terms of cost.

In conventional techniques using a tag peptide and an antibody thereagainst, the antigen (tag peptide)-antibody interaction is so strong that it is not easy to elute antigens from an immunoaffinity column once the antigens bind to antibodies thereagainst. For this reason, in affinity purification methods for proteins, strong acid (for example, pH 3) or alkaline (for example, pH 10) solutions, protein denaturants (high-concentration urea or guanidine hydrochloride) or the like are usually used as an eluent for antigens. However, the use of these eluents is disadvantageous because they denature or destabilize objective proteins and particularly results in very poor yields of multi-subunit enzymes etc. The use of such eluents has another disadvantage that antibodies used for the purification column cannot be repeatedly used because the antibodies easily deteriorate as well. In the case of the FLAG (registered trademark) system as well, repeated use of antibodies M1 and M2 for purification etc. is limited because of their decline in specificity to the antigen.

Therefore, at this point, no purification system that enables proteins to be isolated and purified in high purity and in an inexpensive and easy manner and can endure repeated use is developed yet.

Non Patent Literature 1

Protein Expression and Purification 41 (2005) 98-105

Non Patent Literature 2

"Advance in Epitope Tagging Strategies", Genetic Engineering & Biotechnology News, Apr. 1, 2007

SUMMARY OF INVENTION

Problem to be Solved by the Invention

An object of the present invention is to provide a novel tag peptide that can be used for a system which enables proteins expressed from cloned genes to be highly purified in an inexpensive and easy manner, and to provide a tag peptide fusion protein in which such a tag peptide is linked to a protein. Another object thereof is to provide a polynucleotide encoding the tag peptide, a recombinant vector containing the polynucleotide, and an antibody against the tag peptide. Yet another object thereof is to provide a protein purification, detection or quantification method which can be performed in an inexpensive and simple manner using the interaction of the tag peptide and an antibody thereagainst, and to provide a kit for protein expression, purification, detection or quantification using the above interaction.

Means for Solving the Problem

The present inventor extensively studied affinity tag systems using tag peptides and anti-peptide antibodies that recognize the respective tag peptides. As a result, the inventor found that a certain antibody (hereinafter sometimes referred to as "P20.1 antibody"), which is prepared against a peptide consisting of the sequence corresponding to the N-terminal 20 residues of the human thrombin acceptor PAR4 (SEQ ID NO: 2: hereinafter sometimes referred to as "P4 peptide"), and a peptide having a recognition sequence for the antibody are applicable to protein affinity purification systems. During further studies, the inventor also found that the P20.1 antibody recognizes the 6 residues (Gly-Tyr-Pro-Gly-Gln-Val: SEQ ID NO: 1) from the C terminus of the N-terminal 20 residues of the human thrombin acceptor PAR4, and that among the 6 residues, tyrosine, glycine and glutamine at position 2, 4 and 5 from the N terminus, respectively, are indispensable for the interaction with the antibody. Further, the inventor found that a tag peptide having multiple repeats of the 6-residue sequence (hereinafter sometimes referred to as "P4 sequence") has an increased affinity for the P20.1 antibody. In this way, the inventor reached the idea that the use of the tag peptide having such a repeated sequence and the P20.1 antibody enables proteins expressed from cloned genes to be highly purified in a single step.

The inventor further examined the conditions for affinity purification, and then found that the interaction of the tag peptide having the above-mentioned repeated sequence and the P20.1 antibody can be easily disrupted by water-miscible organic solvents such as polyols.

In conventional affinity purification systems based on an antigen-antibody interaction, strong acid or alkaline solvents etc. need to be used as an eluent. However, the purification system of the present invention allows use of water-miscible organic solvents such as polyols as an eluent, and thereby protein purification can be achieved under mild conditions. Therefore, objective proteins can be purified without any denaturation or the like, and advantageously this purification system can be repeatedly used since antibodies hardly deteriorate. The inventor found that since water-miscible organic solvents used as the eluent in the purification system of the present invention are inexpensive compared to conventional eluents (for example, an eluent for FLAG (registered trademark), etc.), cost cutting in protein purification can be achieved. The term "eluent" as used herein refers to the substance that has an action by which the antibody and the tag peptide dissociate.

The inventor also found that by use of the tag peptide having the above-mentioned repeated sequence and the antibody, sufficient amounts of high-quality recombinant proteins that are suitable for X-ray crystallography can be obtained in a single purification step. For crystallization, proteins that are extremely pure, chemically uniform and 100% biologically active need to be prepared in units of milligrams. The technique of the present invention is preferable for preparation of proteins for X-ray crystallography.

Furthermore, the inventor found that the tag peptide having the above-mentioned repeated sequence and the antibody can be used for protein detection and quantification. The present inventor further studied and then completed the present invention.

Namely, the present invention relates to the following (1) to (16).

(1) A tag peptide comprising an amino acid sequence represented by the following formula (I):

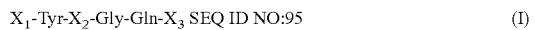

$X_1$-Tyr-$X_2$-Gly-Gln-$X_3$ SEQ ID NO:95      (I)

(wherein $X_1$, $X_2$ and $X_3$ are the same or different and each represent any amino acid residue).

(2) A tag peptide comprising an amino acid sequence represented by the following formula (II):

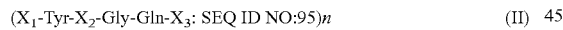

($X_1$-Tyr-$X_2$-Gly-Gln-$X_3$: SEQ ID NO:95)$n$      (II)

(wherein $X_1$, $X_2$ and $X_3$ are the same or different and each represent any amino acid residue; and n represents an integer of 2 to 6).

(3) The tag peptide according to the above (2), wherein the amino acid sequence represented by the formula (II) is an amino acid sequence represented by the following formula (III):

Gly-Tyr-Pro-Gly-Gln-Val: SEQ ID NO:1)$m$      (III)

(wherein m represents an integer of 3 to 5).

(4) The tag peptide according to the above (1) comprising amino acid sequences each represented by the following formula (IV):

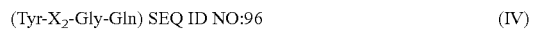

(Tyr-$X_2$-Gly-Gln) SEQ ID NO:96      (IV)

(wherein $X_2$ represents any amino acid residue) at two or more sites.

(5) A tag peptide fusion protein having the tag peptide according to any of the above (1) to (4) linked thereto.
(6) A polynucleotide encoding the tag peptide according to any of the above (1) to (4).

(7) A recombinant vector containing the polynucleotide according to the above (6).
(8) An antibody against the tag peptide according to any of the above (1) to (4).
(9) The antibody according to the above (8) comprising a heavy chain variable region having the amino acid sequence represented by SEQ ID NO: 3 and a light chain variable region having the amino acid sequence represented by SEQ ID NO: 5.
(10) The antibody according to the above (8) which is a single chain antibody having the amino acid sequence represented by SEQ ID NO: 7.
(11) The antibody according to the above (9) which is a monoclonal antibody produced by mouse-mouse hybridoma P20.1 (FERM BP-11061).
(12) A purification method for proteins comprising the following steps (i) to (iii):
(i) a step of preparing a mixture of the tag peptide fusion protein according to the above (5) and another substance;
(ii) a step of allowing the antibody according to any of the above (8) to (11) to act on the mixture obtained in the step (i) and to form a complex with the tag peptide fusion protein; and
(iii) a step of allowing an eluent to act on the complex obtained in the step (ii) for release of the tag peptide fusion protein from the antibody.
(13) The purification method according to the above (12), wherein the eluent is a water-miscible organic solvent.
(14) A detection or quantification method for proteins comprising the following steps (i) to (iii):
(i) a step of preparing a sample containing the tag peptide fusion protein according to the above (5);
(ii) a step of allowing the antibody according to any of the above (8) to (11) to act on the sample obtained in the step (i) and to form a complex with the tag peptide fusion protein; and
(iii) a step of detecting or quantifying the complex obtained in the step (ii).
(15) Mouse-mouse hybridoma P20.1 (FERM BP-11061).
(16) A kit for protein expression, purification, detection or quantification comprising the recombinant vector according to the above (7) or the antibody according to any of the above (8) to (11).

Effect of the Invention

According to the present invention, tag peptide fusion proteins having the above-mentioned tag peptide linked thereto can be highly purified in an easy manner using the interaction of the tag peptide and an antibody thereagainst. Therefore, according to the present invention, even an unskilled person can easily purify unstable recombinant proteins that are expressed from cloned genes in only small amounts. In addition, since the eluent used for purification in the present invention is relatively inexpensive and allows repeated use of antibodies, cost cutting in protein purification can be achieved. Furthermore, the use of the tag peptide and an antibody thereagainst enables efficient detection and/or quantification of tag peptide fusion proteins having the tag peptide linked thereto.

BRIEF DESCRIPTION OF DRAWINGS

FIG. 1 schematically shows tag peptide fusion proteins (P4-Fn) each having a different length of the P4 peptide sequence attached to the N or C terminus of the 9th to 10th region of the Fn3 domain of human fibronectin (Fn9-10).

FIG. 2 (*b*) schematically shows constructs having 1, 3 or 5 repeats of the P4 sequence (6 residues) downstream of the fibrinogen γ chain fragment (γC) following the biotin acceptor sequence (BAS) linked to the hGH minigene.

FIG. 3 shows a partial sequence of the DNA encoding the tag peptide fusion protein having the P4 sequence attached thereto (hGH-BAS-γC-P4), and a partial amino acid sequence of the fusion protein.

FIG. 4 (*a*) shows a partial sequence of the DNA encoding the tag peptide fusion protein having the P4 sequences attached thereto (hGH-BAS-γC-P4×3), and a partial amino acid sequence of the fusion protein.

FIG. 4 (*b*) shows a partial sequence of the DNA encoding the tag peptide fusion protein having the P4 sequences attached thereto (hGH-BAS-γC-P4×5), and a partial amino acid sequence of the fusion protein.

FIG. 5 shows the responsiveness to the monoclonal antibody (P20.1 antibody) of the fusion proteins of Fn with the P4 peptide or its partial peptide based on the ELISA results.

FIG. 6 shows the responsiveness to P20.1 antibody of the fusion proteins of Fn with a modified tag peptide having substitution of alanine for one amino acid residue of the 6-residue P4 sequence (Ala mutants) based on the ELISA results.

FIG. 7 (*b*) shows the affinity for Flag-Fn of a commercially available anti-Flag antibody M2 based on the results of the surface plasmon resonance analysis using Biacore.

Figure 2B:
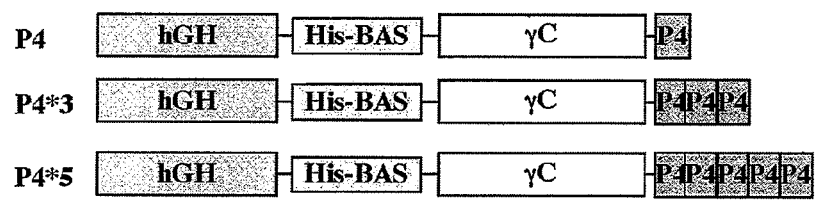
FIG. 2 (*a*) schematically shows a vector for animal cells to express the P4-sequence-tagged fusion protein of the human growth factor (hGH) and the human fibrinogen γ chain C domain.

FIG. 9 is the results showing the P4 peptide-tagged protein (P4(20)-Fn) is detected by western blotting using the P20.1 antibody.

FIG. 10 is a schematic view showing the outline of the phage display method.

FIG. 11 schematically shows the phagemid constructed for preparation of a phage display library.

FIG. 12 shows the examination results on the pattern of the peptide recognition sequence for the P20.1 antibody. FIG. 12 shows SEQ ID NOs:44-93, respectively.

FIG. 13 shows the DNA/amino acid sequences of the heavy chain variable region of the P20.1 antibody Fab fragment.

FIG. 14 shows the DNA/amino acid sequences of the light chain variable region of the P20.1 antibody Fab fragment.

FIG. 15 is a schematic view showing the crystallized complex of the P20.1 antibody Fab fragment and the P4(C8) peptide (left), and an enlarged view of the crystallized complex.

FIG. 16 is an enlarged view in the vicinity of the binding site between the P4(C8) peptide and the P20.1 antibody Fab fragment based on the X-ray crystallography.

FIG. 17 shows the DNA/amino acid sequences of the single chain Fv fragment (scFV) of the P20.1 antibody.

FIG. 18 is a schematic view showing the construct that enables scFv tetramer formation.

FIG. 19 (*a*) shows the peptide binding capacity of the P20.1 antibody Fab fragment based on the test results with Biacore using the P4(20)-Fn-immobilized sensor chip.

FIG. 19 (*b*) shows the peptide binding capacity of the ScFv based on the test results with Biacore using the P4(20)-Fn-immobilized sensor chip.

FIG. 19 (*c*) shows the peptide binding capacity of the scFv tetramer based on the test results with Biacore using the P4(20)-Fn-immobilized sensor chip.

FIG. 20 (*a*) is the measurement results showing the affinity for the antibody of the tag peptide fusion protein having one repeat of the P4 sequence.

FIG. 20 (*b*) is the measurement results showing the affinity for the antibody of the tag peptide fusion protein having 3 repeats of the P4 sequence.

FIG. 20 (*c*) is the measurement results showing the affinity for the antibody of the tag peptide fusion protein having 5 repeats of the P4 sequence.

FIG. 21 shows that the P4 sequence or repeats thereof are detected by the sandwich ELISA using the P20.1 antibody as a detection antibody.

FIG. 22 shows that the P4 sequence or repeats thereof are detected by the sandwich ELISA using the P20.1 antibody as a capture antibody.

FIG. 23 (*a*) shows the examination results on elution conditions of the (P4 sequence×3)-tagged protein from P20.1 antibody-immobilized beads.

FIG. 23 (*b*) shows the examination results on elution conditions of the (P4 sequence×3)-tagged protein from P20.1 antibody-immobilized beads.

FIG. 24 shows a partial sequence of the DNA encoding the F-spondin-(P4 sequence×3) fusion protein and a partial amino acid sequence of the fusion protein.

FIG. 25 shows the analysis results of SDS gel electrophoresis for F-spondin purified with beads having the antibody of the present invention immobilized thereonto.

FIG. 26 is an enlarged image of the crystal of the purified F-spondin.

FIG. 27 is an (partial) electron density map obtained at a resolution of 1.45 Å for F-spondin.

FIG. 28 schematically shows the expression construct for the fusion protein tagged with (P4 sequence×3) to the N terminus of reelin.

FIG. 29 shows the analysis results of SDS gel electrophoresis and western blotting for reelin protein purified with a P20.1 antibody column.

FIG. 30 schematically shows the expression construct for the tag peptide/fibronectin fusion protein, which has the tag sequence having 4 repeats of the 4-residue YPGQ (SEQ ID NO:18).

FIG. 31 shows the electrophoresis results on the tag peptide/fibronectin fusion protein, which has the tag sequence having 4 repeats of the 4-residue YPGQ (SEQ ID NO:18).

FIG. 32 shows the kinetics analysis based on the surface plasmon resonance for the tag peptide/fibronectin fusion proteins, which have the tag sequence having 1 to 5 repeats of the 4-residue YPGQ (SEQ ID NO:18).

FIG. 33 schematically shows the expression construct for the tag peptide fusion protein having (P4 sequence×3) attached to the N terminus of the fluorescence protein GFPuv.

FIG. 34 shows the results of repeated purification of the GFPuv protein using P20.1 antibody-Sepharose.

BEST MODE FOR CARRYING OUT THE INVENTION

Tag Peptide

The tag peptide of the present invention has an amino acid sequence represented by the following formula (I):

$$X_1\text{-Tyr-}X_2\text{-Gly-Gln-}X_3 \text{ SEQ ID NO:95} \quad (I)$$

(wherein $X_1$, $X_2$ and $X_3$ are the same or different and each represent any amino acid residue). The tag peptide of the present invention may have an amino acid sequence represented by the following formula (II):

($X_1$-Tyr-$X_2$-Gly-Gln-$X_3$: SEQ ID NO:95)$n$     (II)

(wherein $X_1$, $X_2$ and $X_3$ are the same or different and each represent any amino acid residue; and n represents the integer of 2 to 6).

Further, it is preferable that the tag peptide of the present invention has an amino acid sequence represented by the above formula (I) (hereinafter sometimes referred to as "sequence (I)") and has amino acid sequences each represented by the following formula (IV):

(Tyr-$X_2$-Gly-Gln) SEQ ID NO:96     (IV)

(wherein $X_2$ represents any amino acid residue) at two or more sites.

For example, in a tag peptide having 2 repeats of sequence (I), amino acid sequences each represented by formula (IV) (hereinafter sometimes referred to as "sequence (IV)") are located at two sites so that they flank two amino acid residues $X_3$ and $X_1$. In a tag peptide having 3 repeats of sequence (IV), one sequence (I) in which $X_1$ is Gln and $X_3$ is Tyr is included. In a tag peptide having sequences (IV) at two or more sites, the sequences (IV) are located at least two sites of a tag peptide having at least one sequence (I) and the interval or location of the sequences (IV) are not limited.

In the sequence (I), $X_1$ is not particularly limited, but glycine is preferable, for example. $X_2$ is preferably an amino acid having a small side chain, such as serine, valine, cysteine, alanine, threonine, glutamic acid, glycine and aspartic acid, or proline. More preferred is proline. $X_3$ is preferably a hydrophobic amino acid, and examples thereof include valine, leucine, isoleucine, alanine, phenylalanine, tyrosine, tryptophan, proline and methionine. Inter alia, valine is preferable. The sequence (I) is particularly preferably Gly-Tyr-Pro-Gly-Gln-Val (SEQ ID NO: 1). Constituent amino acids of the tag peptide of the present invention are all L-amino acids.

The tag peptide of the present invention may consist of sequence (I) only, or comprise sequence (I) and other amino acid residues. The tag peptide preferably comprises sequences (I) at two or more sites, and more preferably comprises an amino acid sequence having 2 repeats or more of sequence (I). When the tag peptide comprises sequences (I) at two or more sites, the number of the sequence (I) is not limited. Also when the tag peptide comprises an amino acid sequence having 2 repeats or more of sequence (I), the repeat number is not limited. It is confirmed that the tag peptide of the present invention has a higher affinity for an antibody thereagainst as the repeat number of sequence (I) increases. The maximum number of amino acid residues of the tag peptide of the present invention is not particularly limited, but in respect of practical use, preferably 50 or less, more preferably 40 or less and even more preferably 30 or less.

It is particularly preferable that the tag peptide of the present invention comprises an amino acid sequence having 3 to 5 repeats of the following repeat unit;
Gly-Tyr-Pro-Gly-Gln-Val (SEQ ID NO: 1; sometimes referred to as "P4 sequence"), or
the following repeat unit;
Tyr-Pro-Gly-Gln (SEQ ID NO: 18).

The tag peptide of the present invention can be linked to any protein by a genetic engineering method, and thereby can be formed into a fusion protein of the tag peptide and any protein. In this case, the tag peptide may be linked to the N or C terminus of any protein. Such a tag peptide fusion protein in which the tag peptide is linked to the N or C terminus of any protein can be highly purified in a single step by use of an antibody that specifically binds to the tag peptide. Using the antibody, detection of the tag peptide fusion protein, quantification thereof, etc. can also be performed.

The tag peptide of the present invention can be chemically linked to any substance. Using an antibody that specifically binds to the tag peptide of the present invention, a substance that the tag peptide is chemically linked to can be highly purified in a simple manner, and its detection, quantification, etc. can also be performed. The substance that the tag peptide is chemically linked to is not limited, and examples thereof include proteins, nucleic acids, saccharides, organic polymers and metals.

[Tag Peptide Fusion Protein]

The tag peptide fusion protein of the present invention refers to a fusion protein of the tag peptide of the present invention set forth above (hereinafter referred to simply as "tag peptide") and any protein, in which they are linked to each other. In the tag peptide fusion protein of the present invention, the tag peptide may be linked to the N or C terminus of any protein. Such a tag peptide fusion protein in which the tag peptide is linked to the N or C terminus of any protein can be highly purified in a single step by use of an antibody that specifically binds to the tag peptide.

The tag peptide fusion protein of the present invention can be prepared by a known gene-recombination technology. The outline is illustrated as follows.

First, a polynucleotide encoding the tag peptide of the present invention is synthesized by a known method. The polynucleotide may be DNA or RNA, and is preferably DNA. When the polynucleotide is DNA, it can be synthesized with a DNA synthesizer. Also, DNA fragments separately synthesized may be ligated. The DNA sequence for the tag peptide may be diverse due to degeneracy of the genetic code, and is not particularly limited as long as a peptide expressed from the DNA sequence has an amino acid sequence of the tag peptide of the present invention. As DNA encoding the P4 sequence, the DNA sequence represented by SEQ ID NO: 9 can be used, for example. SEQ ID NO: 11 is an example of DNA encoding a tag peptide consisting of the amino acid sequence having 3 repeats of the P4 sequence, and SEQ ID NO: 13 is an example of DNA encoding a tag peptide consisting of the amino acid sequence having 5 repeats of the P4 sequence.

Next, DNA encoding an objective protein is ligated to the 3'- or 5'-terminus of the synthesized DNA encoding the tag peptide. Alternatively, when DNA encoding the objective protein is prepared by PCR or other methods, the use of the DNA encoding the tag peptide as a 3'- or 5'-end primer gives the gene of the objective protein ligated with the DNA encoding the tag peptide as a PCR product.

In the tag peptide fusion protein of the present invention, a spacer peptide may be inserted between the objective protein and the tag peptide. The spacer peptide may be any peptide that does not bind to or associate with the antibody against the tag peptide of the present invention, which is described below, and does not impair the interaction of the tag peptide and the antibody. Examples of the spacer peptide include peptides having a protease recognition sequence. For insertion of the spacer peptide, DNA preparation is performed such that DNA encoding the spacer peptide is ligated between the DNA encoding the tag peptide and the DNA encoding the object protein.

After the DNA preparation, the obtained DNA, which comprises DNA encoding the tag peptide and DNA encoding the objective protein, is appropriately inserted into an expression vector. The vector is not particularly limited, and known expression vectors derived from bacteria, yeasts, viruses or the like can be preferably used. A promoter in the expression vector is any promoter compatible with hosts used for expression. The expression vector may further comprise an enhancer, a splicing signal, a poly A addition signal, a selection marker and a replication origin. The thus-obtained expression vector is introduced into host cells. The host cell is not particularly limited, and examples thereof include microorganisms such as *Escherichia coli* and yeasts; and animal cells. Preferred are animal cells. A method of introducing the expression vector into host cells can be appropriately selected from known transformation methods depending on the kind of host cells. The obtained recombinant microorganisms or cells are cultured in an appropriate medium for expression of the tag peptide fusion protein. The tag peptide fusion protein may be purified from the recombinant microorganisms or cells, or culture media therefor in a single step by use of an antibody described below.

The present invention also includes the polynucleotide encoding the tag peptide, and a recombinant vector containing the polynucleotide, both of which are illustrated in the above preparation of the tag peptide fusion protein. The recombinant vector of the present invention is not limited to recombinant vectors that enable expression of the fusion protein of the tag peptide and the objective protein (tag peptide fusion protein), and includes vectors just containing the polynucleotide encoding the tag peptide.

[Antibody]

The present invention provides an antibody against the tag peptide of the present invention. The antibody of the present invention is not particularly limited as long as it recognizes the tag peptide of the present invention and specifically interacts therewith. An exemplary antibody of the present invention recognizes tyrosine, glycine and glutamine at position 2, 4 and 5 from the N terminus of sequence (I), respectively, and interacts with the tag peptide of the present invention. Specifically, in the antigen binding site of such an antibody, there exist hydrophobic interaction between the tyrosine of sequence (I) in the tag peptide and tryptophan in the antibody, hydrophobic interaction between the alpha carbon of the glycine of sequence (I) and Trp50 of the antibody H chain, a hydrogen bond between a nitrogen atom of the glutamine of sequence (I) and a carbonyl oxygen of the main chain in the antibody H chain, and a hydrogen bond between an oxygen atom of the glutamine of sequence (I) and an amide nitrogen atom of the main chain in the antibody H chain. Such a peptide-antibody interaction is exemplified by FIG. 16, which shows an example of the specific conformation of amino acid residues in the peptide-antibody binding site based on X-ray crystallography.

Specific examples of the antibody include antibodies obtained by immunization of mammals such as mice and rabbits with a peptide antigen corresponding to the N-terminal 20 residues of the human thrombin receptor PAR4. More specifically, preferable examples thereof include (a) an antibody comprising a heavy chain variable region having the amino acid sequence represented by SEQ ID NO: 3 and a light chain variable region having the amino acid sequence represented by SEQ ID NO: 5; and (b) a single chain antibody having the amino acid sequence represented by SEQ ID NO: 7.

An example of the antibody (a) is a monoclonal antibody produced by mouse-mouse hybridoma P20.1 (internationally deposited at International Patent Organism Depositary, National Institute of Advanced Industrial Science and Technology (central 6, 1-1-1, Higashi, Tsukuba-shi, Ibaraki-ken, 305-8566, Japan) under the accession number FERM BP-11061 on Dec. 11, 2007). The Fab fragment obtained by digestion of this monoclonal antibody with papain is also included in the antibody (a). The antibody (b) is a single chain antibody obtained from the variable region of the antibody (a). Preferably, the single chain antibody (b) is used as a dimer to a tetramer, the formation of which is permitted by gene-recombination technology etc.

The antibody (a) can be prepared, for example, from mouse-mouse hybridoma P20.1 (FERN BP-11061) as described in the examples below. The mouse-mouse hybridoma P20.1 (FERN BP-11061), which produces the antibody of the present invention, is also one aspect of the present invention.

The antibodies (a) and (b) can also be prepared by gene-recombination technology. For preparation of the antibody (a) by gene-recombination technology, DNA encoding the amino acid sequence represented by SEQ ID NO: 4 (SEQ ID NO: 3) and DNA encoding the amino acid sequence represented by SEQ ID NO: 6 (SEQ ID NO: 5) are synthesized first. For preparation of the antibody (b) by gene-recombination technology, DNA encoding the amino acid sequence represented by SEQ ID NO: 8 (SEQ ID NO: 7) is synthesized first. In each case, the DNA(s) is(are) inserted into an appropriate expression vector, which is then introduced into host cells for protein expression. Subsequently, isolation and purification of the expressed protein give the antibody (a) or (b).

[Purification Method for Proteins]

The present invention provides a purification method for proteins using the antibody of the present invention. The purification method for proteins comprises the following steps (i) to (iii):

(i) a step of preparing a mixture of the tag peptide fusion protein and another substance;

(ii) a step of allowing the antibody of the present invention to act on the mixture obtained in the step (i) and to form a complex with the tag peptide fusion protein; and (iii) a step of allowing an eluent to act on the complex obtained in the step (ii) for release of the tag peptide fusion protein from the antibody.

Since the antibody of the present invention specifically interacts with the tag peptide of the tag peptide fusion protein of the present invention, use of the antibody enables the tag peptide fusion protein to be highly purified in a single step.

In the step (i), a method of preparing the mixture is not particularly limited. For example, when the objective protein, i.e., the tag peptide fusion protein is present in cells, lysis, homogenization, etc. of cultured recombinant microorganisms or cells by a known method gives the desired mixture (cell lysate) containing the tag peptide fusion protein and another substance. When the tag peptide fusion protein is present in an insoluble fraction such as an inclusion body, solubilization and subsequent refolding (unwinding) of proteins, etc. may be appropriately performed before the step (ii). When the tag peptide fusion protein is secreted from cells into a culture medium, the supernatant of the culture medium is collected for use as a mixture in the step (ii). Solids contained in the cell lysate or supernatant are removed by centrifugation, and if needed the pH of the lysate or supernatant is adjusted to neutrality (7 to 8), but addition of salts or other substances is not particularly needed. The concentration of the objective protein in the mixture is preferably 0.2 µg/mL or more.

In the step (ii), use of an immobilized antibody, i.e., the antibody of the present invention immobilized onto a support, is preferable. The support onto which the antibody is immobilized is not particularly limited as long as the effect of the present invention is achieved, and known supports can be used. For example, Sepharose (GE Healthcare), Affi-Gel (BIO-RAD), etc. are preferable. A method of immobilizing the antibody onto the support is not particularly limited and can be appropriately selected depending on the kind of the support, etc. For example, for immobilization of the antibody onto Sepharose, the antibody is dialyzed against a coupling buffer and then mixed with CNBr-activated Sepharose (GE Healthcare) at room temperature for about 1 to 2 hours.

Examples of the purification method for proteins in the present invention include both of a column method using the above-mentioned immobilized antibody packed into a column, and a batch method involving mixing the immobilized antibody with a sample for complex formation in a suspension. In the former method, the immobilized antibody is packed into a column, the mixture prepared in the step (i) is loaded onto the column, and thereby the antibody of the present invention acts on the tag peptide. In this way, the tag peptide and the antibody bind to each other and thereby a complex of the tag peptide fusion protein and the antibody is formed. In the latter method, about 100 μL of the immobilized antibody is gently mixed with 10 mL of a sample solution. After a complex of the tag peptide fusion protein and the antibody is formed in the mixture, the mixture is packed into a column.

Then, in the step (iii), the eluent is allowed to act on the complex obtained in the step (ii) for release of the tag peptide fusion protein from the antibody. Namely, by an action of the eluent on the complex, the antibody and the tag peptide dissociate, and the tag peptide fusion protein bound to the immobilized antibody via the tag peptide is released from the antibody.

As the eluent, any substance that has an action to disrupt the bond between the tag peptide and the antibody can be used. Examples of such a substance include water-miscible organic solvents such as polyols, and the tag peptide of the present invention. In the purification method for proteins of the present invention, the eluent can be appropriately selected depending on the kind of the objective protein, etc., but is preferably a water-miscible organic solvent. Inter alia, particularly preferred is propylene glycol or dimethyl sulfoxide. Ethylene glycol can also be used.

When the eluent is allowed to act on the complex of the tag peptide fusion protein and the antibody, it is preferable that the eluent is dissolved in water or an appropriate buffer solution and that the resulting elution solution is loaded onto the column. In this case, the tag peptide fusion protein released from the antibody by an action of the eluent is eluted together with the elution solution from the column. Water or a buffer solution may be selected depending on the kind of the protein.

Preferably, the content of the eluent in the elution solution is appropriately varied with the kind of the eluent or the objective protein, i.e., the tag peptide fusion protein, or the like. For example, when a water-miscible organic solvent is used as the eluent, the blending ratio of the water-miscible organic solvent is preferably about 40% (v/v) or more relative to the total volume of water or a buffer solution, and the water-miscible organic solvent, the total volume being set to 100%. Alternatively, the volume ratio of water or a buffer solution to the water-miscible organic solvent (water or buffer solution:water-miscible organic solvent) is preferably about 60:40 to 40:60.

When the tag peptide is used as the eluent, the elution solution is preferably prepared so that the concentration of the tag peptide is about 0.1 to 1 mg/mL in water or a buffer solution. As the tag peptide used as the eluent, the tag peptides of the present invention can be used without limitation, but the tag peptide comprising sequence (I) is preferred. The tag peptide of the present invention can be prepared by a known peptide synthesis method.

To the elution solution, a salt may be added in order to stabilize the tag peptide fusion protein to be obtained. The kind of the salt can be determined according to the kind of the protein, etc., and is not particularly limited. The concentration of the salt can be appropriately adjusted depending on the kind of the protein, and is not particularly limited.

After purification of the tag peptide fusion protein, the immobilized antibody is washed with the elution solution and thereby can be used repeatedly.

The purification method for proteins of the present invention may further comprises a step (iv) of cleaving the tag peptide from the tag peptide fusion protein after the steps (i) to (iii) are all completed. For example, when the spacer peptide having a protease recognition sequence is inserted between the tag peptide and the objective protein, a protease that recognizes the protease recognition sequence is allowed to act on the purified fusion protein under appropriate conditions, and thereby the object protein without the tag peptide can be obtained.

In the purification method for proteins of the present invention, the tag peptide and the antibody specifically interact with each other and the interaction is easily disrupted by an action of the eluent such as water-miscible organic solvents. Thus, the tag peptide fusion protein can be highly purified in a single step. Further, the purification can be performed without any denaturation of the objective fusion protein or the antibody since a water-miscible organic solvent etc. is used as the eluent in the purification method. Therefore, according to the present invention, sufficient amounts of high-quality recombinant proteins that are suitable for X-ray crystallography can be obtained in a single purification step. For crystallization, proteins that are extremely pure, chemically uniform and 100% biologically active need to be prepared in units of milligrams. The technique of the present invention is preferable for preparation of proteins that can be subjected to X-ray crystallography.

Furthermore, in the purification method for proteins of the present invention, the immobilized antibody can be repeatedly used for purification. In fact, the present inventor repeatedly used an immobilized antibody, i.e., the P20.1 antibody immobilized onto Sepharose, for purification of the tag peptide fusion protein (GFPuv-P4×4 fusion protein) of the present invention and examined the effect of its repeated use on the purification. The inventor confirmed that even though the immobilized antibody was repeatedly used 21 times, the yield of the fusion protein declined only slightly (see [10] of Examples). Furthermore, since water-miscible organic solvents used as the eluent are relatively inexpensive, the purification method of the present invention enables proteins to be purified in an inexpensive and simple manner.

[Detection or Quantification Method for Proteins]

The present invention provides a detection or quantification method for proteins using the antibody of the present invention. The detection or quantification method for proteins comprises the following steps (i) to (iii):

(i) a step of preparing a sample containing the tag peptide fusion protein;
(ii) a step of allowing the antibody to act on the sample obtained in the step (i) and to form a complex with the tag peptide fusion protein; and
(iii) a step of detecting or quantifying the complex obtained in the step (ii).

Since the antibody of the present invention specifically interacts with the tag peptide of the tag peptide fusion protein, use of the antibody enables the tag peptide fusion protein to be detected or qualified.

The detection or quantification method for proteins of the present invention can be applied to various immunological techniques such as western blotting, sandwich ELISA, flow cytometry, immunoprecipitation and immunohistochemistry.

In the step (i) of the detection or quantification method for proteins, a method of preparing the sample is not particularly limited. For example, the sample containing the tag peptide fusion protein can be prepared by lysis or homogenization of cells expressing the objective protein, i.e., the tag peptide fusion protein.

As for the step (ii) of allowing the antibody to act on the sample obtained in the step (i) and to form the complex with the tag peptide fusion protein, and the step (iii) of detecting or quantifying the complex, the respective procedures will be illustrated below by citing, as an example, the case of sandwich ELISA or western blotting.

(A) Sandwich ELISA

In the sandwich ELISA, the antibody of the present invention can be used as a detection antibody or a capture antibody for detection or quantification of the tag peptide fusion protein.

(A-1) Case where the Antibody of the Present Invention is Used as a Detection Antibody
(1) The antibody of the present invention is modified or labeled by some method in advance. The modifying or labeling method is not particularly limited, and examples thereof include biotinylation, enzyme labeling (such as peroxidase labeling), fluorochrome labeling (such as fluorescein labeling) and radioisotope labeling (such as 125I labeling).
(2) Apart from the antibody of the present invention, another antibody that specifically interacts with a protein region other than the tag peptide in the fusion protein is prepared and then immobilized onto microtiter plates.
(3) The sample obtained in the step (i) is added over the immobilized antibody of the step (2) and this antibody is allowed to capture the tag peptide fusion protein.
(4) Then, the antibody of the present invention is allowed to act on the tag peptide fusion protein captured as above and to form a complex with the tag peptide fusion protein. In the case where the antibody of the present invention is enzyme-labeled, the step (6) is performed next.
(5) In the case where the antibody of the present invention is biotinylated, enzyme-labeled streptavidin is allowed to act on the complex and to bind to the biotin of the antibody.
(6) The corresponding chromogenic or luminescent substrate for the enzyme (for example, when the enzyme is peroxidase, the substrate is ABTS) is added. The enzyme catalyzes the cleavage of the substrate to yield a colored reaction product. By measuring the absorbance for each sample, the complex of the tag peptide fusion protein and the antibody can be detected. Since the absorbance is quantitatively correlated with the amount of the tag peptide fusion protein in the sample, the complex of the fusion protein and the antibody can be quantified. In this case, combined use of a substrate enhancer with the chromogenic substrate can raise detection sensitivity.

(A-2) Case where the Antibody of the Present Invention is Used as a Capture Antibody
(1) The antibody of the present invention is immobilized onto microplates etc.
(2) The sample obtained in the step (i) is added over the immobilized antibody, and this antibody is allowed to capture the fusion protein and to form a complex with the fusion protein.
(3) An antibody that specifically interacts with a protein region other than the tag peptide in the fusion protein is allowed to act on the complex obtained in the above (2) and to bind to the complex.
(4) In the case where the antibody allowed to act on the complex in the above (3) is not labeled with any enzyme, an antibody that specifically reacts with the antibody added in the above (3) (enzyme-labeled antibody:secondary antibody) is allowed to further act on the reaction mixture.
(5) After addition of the corresponding substrate for the enzyme (usually a chromogenic or luminescent substrate), an enzyme reaction product is detected.

(B) Western Blotting

In the western blotting, the complex is detected as follows.
(1) The sample obtained in the step (i) is subjected to SDS electrophoresis for separation of the tag peptide fusion protein, and separated proteins are transferred onto a nitrocellulose membrane or a PDVF membrane.
(2) The antibody of the present invention is allowed to act on the fusion protein on the membrane and to form a complex therewith. In the case where the antibody is enzyme-labeled, the step (4) is performed next.
(3) In the case where the antibody allowed to act on the complex in the above (2) is not labeled with any enzyme, an antibody that specifically reacts with the antibody added in the above (2) (enzyme-labeled antibody:secondary antibody) is allowed to further act on the reaction mixture.
(4) After addition of the corresponding substrate for the enzyme (usually a chromogenic or luminescent substrate), an enzyme reaction product is detected.

The antibody and tag peptide fusion protein of the present invention are applicable to the fluorescent antibody method, the immunoprecipitation method, etc. as well as development of detection reagents, cellular imaging, sensor development, etc.

[Kit]

The present invention provides a kit for protein expression, purification, detection or quantification. The kit comprises the recombinant vector or antibody of the present invention. By use of the kit of the present invention, protein expression, purification, detection or quantification can be simply performed. The kit for protein expression essentially comprises the recombinant vector of the present invention, and the kit for protein purification, detection or quantification essentially comprises the antibody of the present invention. Preferably, the kit of the present invention comprises both the recombinant vector and antibody of the present invention.

The recombinant vector of the kit is preferably provided in such a form that users of the kit can prepare an expression vector for a tag peptide fusion protein in which the tag peptide of the present invention and an objective protein are linked to each other by inserting DNA encoding the objective protein into vectors. Then, the users can simply achieve expression of the desired protein, i.e., the tag peptide fusion protein by introducing the prepared expression vector into appropriate host cells and culturing the host cells.

It is preferable that the antibody of the kit is immobilized onto an appropriate support (in the case of the kit for protein purification), or appropriately labeled (enzyme labeling, radioactive labeling, fluorescent labeling, etc.) or modified (biotinylation etc.) (in the case of the kit for protein detection or quantification). When the kit is used for protein purification, detection or quantification, the purification method for proteins of the present invention and the detection or quantification method for proteins of the present invention can be employed.

The kit may further comprises a secondary antibody, a reaction buffer solution, a substrate, an instruction manual, etc. in addition to the recombinant vector or antibody of the present invention.

Advantages of the Present Invention

The tag system of the present invention is advantageous in respect of the followings.
(I) The tag peptide has a short recognition sequence and none of charged amino acids, which cause nonspecific binding.
(II) The interaction between the target tag sequence and the corresponding antibody (P20.1 antibody) has such an affinity that protein purification can be performed in a single step.
(III) Since the interaction set forth in the above (II) is disrupted on conditions that do not affect proteins (for example, 40% ethylene glycol etc.), high-quality antigen purification and repeated use of a column are practicable at the same time.
(IV) Since the atomic level resolution 3D structure of the complex of the antibody and the tag peptide is already determined, further modification and improvement of the tag system are possible.
(V) The tag system can be applied to immunoblotting, the fluorescent antibody method, the immunoprecipitation method, etc., and has high potential for application not only to protein purification, but also to development of detection reagents, cellular imaging and sensor development.

Among the above (I) to (V), the advantage (III) cannot be found in any protein purification system using commercially available mass-produced antibodies.

EXAMPLES

Next, the present invention will be illustrated in detail by examples, but is not limited thereto.
[1] Monoclonal Antibody Preparation
An anti-PAR4 peptide antibody was prepared by a usual method as follows.
(1-1) Peptide Synthesis and Peptide Immunization
A peptide having the following sequence (SEQ ID NO: 2): NH$_2$-GGDDSTPSILPAPRGYPGQVC-COOH, which corresponds to the N-terminal 20 residues of the human thrombin receptor PAR4, was synthesized by the Fmoc solid phase method.

The above-mentioned peptide was purified by reversed phase HPLC and then coupled to keyhole limpet hemocyanin (KLH), which is a carrier protein, via a cysteine (Cys) residue and the resulting complex was used as an immunogen.

A Balb/c mouse was immunized with the resulting peptide-KLH complex and an adjuvant, and antibody titer measurement was performed by the ELISA method. Repeated immunization (25 μg×5) gave a high titer antibody. Spleen cells of this mouse were used for cell fusion.
(1-2) Cell Fusion and Hybridoma Establishment
B cells were separated from the spleen cells and fused with mouse myeloma cells (SP2/0 cell line) by the polyethylene glycol method, and then cell culture was performed in an HAT selection medium.

ELISA-based screening was performed using the supernatants of wells where a colony was found, and strongly positive samples were selected as a candidate for secondary screening.

In the secondary screening, a fusion protein (PAR4-Fn) described later was used as an antigen. As a result, one highly responsive clone was obtained. The clone was subjected to cloning by limiting dilution, and finally, mouse-mouse hybridoma P20.1 was established (internationally deposited at International Patent Organism Depositary, National Institute of Advanced Industrial Science and Technology (central 6, 1-1-1, Higashi, Tsukuba-shi, Ibaraki-ken, 305-8566, Japan) under the accession number FERM BP-11061 on Dec. 11, 2007).
(1-3) Antibody Purification, Fab Fragment and Preparation of Antibody Immobilized onto Sepharose
(1) Antibody Purification
The mouse-mouse hybridoma P20.1 (FERM BP-11061) established in the (1-2) was cultured in a RPMI1640 medium supplemented with 10% fetal bovine serum. From the cell culture supernatant, a P20.1 antibody was purified by use of protein A sepharose. The purified antibody was an IgG1 isotype and has λ light chains.
(2) Fab Fragment
The Fab fragment of the P20.1 antibody was prepared by use of an Immunopure Fab preparation kit commercially available from PIERCE. In detail, the purified P20.1 antibody (IgG) was digested with immobilized papain at 37° C. for 16 hours, the digest was loaded onto protein A sepharose, and unbound digest was subjected to gel filtration for purification.
(3) Preparation of Antibody Immobilized onto Sepharose
The purified P20.1 antibody (about 30 mg) was dialyzed against a coupling buffer (0.1 M NaHCO$_3$, 0.3 M NaCl, pH 8.3) and then mixed with CNBr-activated Sepharose 4B (GE Healthcare), which was washed with 1 mM hydrochloric acid in advance, at room temperature for 1 hour, to give an antibody immobilized onto Sepharose. Unreacted active groups were blocked with 0.1M Tris, and nonspecifically bound antibodies were removed with 0.1 M Gly-HCl, pH 2.2. The results of qualitative analysis of the unbound antibody showed that about 2 mg of the P20.1 antibody per 1 mL of Sepharose resin was able to be immobilized.
[2] Preparation of Tag Peptide Fusion Protein
(2-1) Preparation of Tag Peptide/Fibronectin Fusion Protein
Using a construct which expresses the 9th to 10th region of the Fn3 domain of human fibronectin (185 residues), constructs for 6 different tag peptide fusion proteins (6 sequences from the top in FIG. 1) were prepared. Each fusion protein has a different length of the P4 peptide sequence (the whole or a part of the N-terminal 20 residues of PAR4) attached to the N or C terminus of the above domain. The insert was prepared by extension PCR and then was inserted into the NdeI-BamHI site of the expression vector pET11c (Novagen). Constructs for mutants (Ala mutants) (6 sequences from the bottom in FIG. 1) were prepared by use of Quick Change Mutagenesis kit (Stratagen). Each mutant has substitution of alanine for a different amino acid of the C-terminal 6 residues of the P4 peptide sequence.

*Escherichia coli* BL21 (DE3) cells were transformed with the respective constructs described above, and induced expression of the corresponding tag peptide fusion proteins was achieved by a usual method. Each of the produced tag peptide fusion proteins was purified from *Escherichia coli* lysate by anion exchange chromatography.
(2-2) Preparation of Human Growth Factor/Human Fibrinogen/Tag Peptide Fusion Protein
A vector for animal cells to express a fusion protein of human growth factor (hGH) and the C domain of the human fibrinogen γ chain has been already reported (Xiao et al.

Nature 432, 59-67, 2004). To the C terminus of the construct for this fusion protein, DNA encoding a peptide having 1, 3 or 5 repeats of the 6-residue peptide derived from the P4 peptide (GYPGQV: P4 sequence (SEQ ID NO: 1)) was attached by extension PCR, to give the desired DNA. The vector for animal cells to express the P4-sequence-tagged fusion protein of human growth factor (hGH) and the C domain of the human fibrinogen γ chain is shown in FIG. 2 (a). FIG. 2 (b) shows constructs having 1, 3 or 5 repeats of the P4 sequence (6 residues) downstream of the fibrinogen γ chain fragment (γC) following the biotin acceptor sequence (BAS) bound to the minigene of hGH.

A partial sequence of DNA encoding the tag peptide fusion protein having P4 sequence attached thereto (hGH-BAS-γC-P4) is shown in SEQ ID NO: 15 and FIG. 3. In the base sequence shown in SEQ ID NO: 15, the bases at nucleotide positions 1 to 2100 and 3121 to 5424 are omitted from the entire 5424-base DNA encoding the tag peptide fusion protein having the P4 sequence attached thereto (hGH-BAS-γC-P4). Namely, the DNA sequence represented by SEQ ID NO: 15 is the base sequence corresponding to nucleotide positions 2101 to 3120 of the 5424-base DNA encoding hGH-BAS-γC-P4. In FIG. 3, the underlined part is a hGH sequence. The shaded region indicates a His tag sequence. The region in italic type indicates a linker. The thick underlined part indicates a TEV protease site. The part with a dashed line is a BAS sequence. The region in a bold letter is a P4 tag. The boxed amino acid sequence is a P4 sequence. The unmarked region indicates a fibrinogen γC region.

The DNA sequence encoding a tag peptide consisting of the amino acid sequence having 3 repeats of the P4 sequence (P4×3) is shown in SEQ ID NO: 11. The DNA sequence encoding a tag peptide consisting of the amino acid sequence having 5 repeats of the P4 sequence (P4×5) is shown in SEQ ID NO: 13. A partial DNA sequence of the construct having the sequence P4×3 attached thereto is shown in FIG. 4 (a). A partial DNA sequence of the construct having the sequence P4×5 attached thereto is shown in FIG. 4 (b). In the base sequence shown in FIG. 4 (a), the bases at nucleotide positions 1 to 3000 and 3181 to 5460 are omitted from the entire 5460 bases. In the base sequence shown in FIG. 4 (b), the bases at nucleotide positions 1 to 3000 and 3181 to 5496 are omitted from the entire 5496 bases. In FIGS. 4 (a) and 4 (b), the region in a bold letter is a P4 tag, the boxed amino acid sequence is a P4 sequence, and the unmarked region is a fibrinogen γC region.

Each of the prepared plasmids was transfected into a human fibroblast cell line HEK293T, which was then cultured in a DMEM medium supplemented with 10% fetal bovine serum. From the cell culture supernatant, each human growth factor/human fibrinogen/tag peptide fusion protein was purified by Ni-NTA agarose (Qiagen) chromatography. For detection of this tag peptide fusion protein, a mouse anti-hGH monoclonal antibody HGH-B (American Type Culture Collection) and an antiserum (rabbit) against the biotin acceptor sequence (BAS) were used.

[3] Characterization of Monoclonal P20.1 Antibody (3-1) Epitope Analysis

The minimum peptide sequence required for recognition by the P20.1 antibody was identified by the ELISA method using various kinds of P4-Fn proteins prepared in the above (2-1). The protocol is as follows.

(1) A P4-Fn (or a mutant thereof) solution diluted at 10 μg/mL was added at 50 μL/well to 96-well plates, which were then allowed to stand (4° C., 16 hours).

(2) The supernatant of each well was removed with an aspirator, a 1% BSA solution in Tris-buffered saline (TBS; 20 mM Tris-HCl, 150 mM NaCl, pH 7.5) was added at 200 μL/well, and the plates were allowed to stand at room temperature for 1 hour.

(3) A P20.1 antibody solution (2 to 5 μg/mL) was added at 50 μL/well and the plates were allowed to stand at room temperature for 1 hour.

(4) Each well was washed with 200 μL of TBS 3 times.

(5) A peroxidase-labeled anti-mouse IgG (1/1000 dilution) was added at 50 μL/well, and the plates were allowed to stand at room temperature for 30 minutes.

(6) Each well was washed with 200 μL of TBS 4 times.

(7) A peroxidase chromogenic substrate (ABTS) was added at 100 μL/well, the plates were allowed to stand at room temperature for 5 to 10 minute, and then the absorbance of the solution in each well was measured at 405 nm.

The ELISA results showed that the P4 peptide, whether fused to the N or C terminus of the Fn, can be recognized by the P20.1 antibody. The ELISA results of 5 different tag peptide fusion proteins having the P4 peptide attached to the N terminus of the Fn are shown in FIG. 5. These results showed that the C-terminal 6-residue region of the P4 peptide (GYPGQV: P4 sequence (SEQ ID NO: 1)) is enough for recognition by the P20.1 antibody. Each mutant having substitution of Ala for a different amino acid of the 6 residues was similarly examined and the results are shown in FIG. 6. In FIG. 6, "Control" indicates the value of non-coated wells, and "WT" indicates the value of wells coated with the P4(20)-Fn. G, Y, P, G, Q or V represents a modified fusion protein having substitution of alanine for the corresponding amino acid. As is clear from FIG. 6, Y2, G4 and Q5 are essential, but the substitution of Ala for G1, P3 or V6 does not change the responsiveness.

(3-2) Binding Affinity of P20.1 Antibody

Figure 7A:
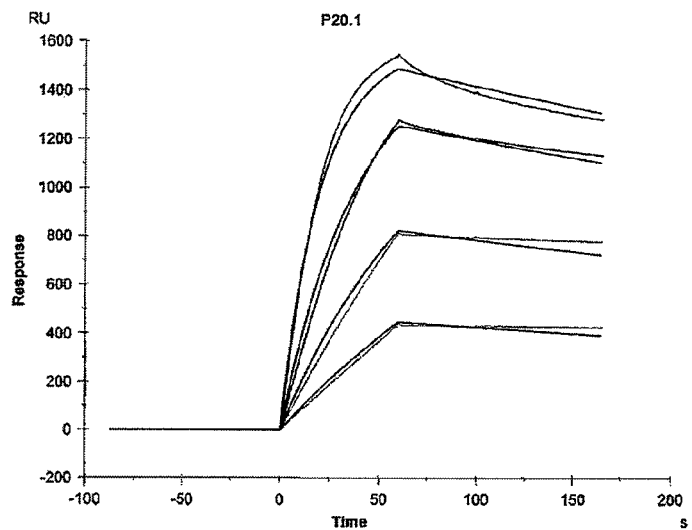
FIG. 7 (*a*) shows the affinity for P4(20)-Fn of the P20.1 antibody based on the results of the surface plasmon resonance analysis using Biacore.
Figure 7B:
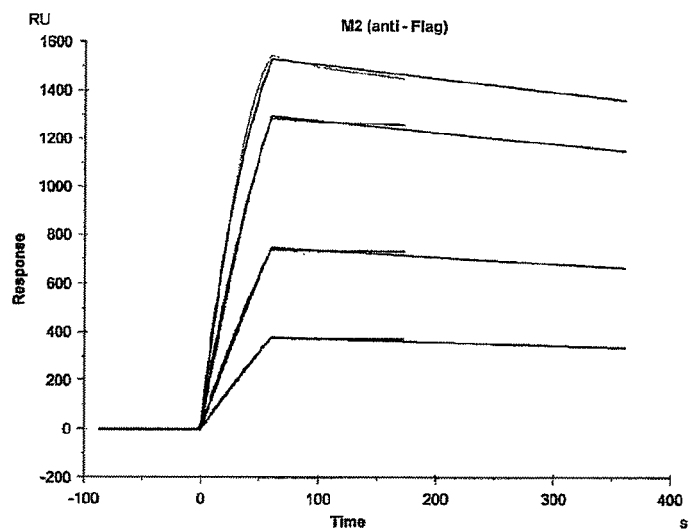

For examination on the binding affinity of the P20.1 antibody for the P4 peptide sequence, the surface plasmon resonance analysis using Biacore was performed. After the P4(20)-Fn (see FIG. 1) purified in the (2-1) was biotinylated and then captured by a streptavidin-immobilized sensor chip, a purified P20.1 antibody was allowed to flow over the prepared sensor chip at various concentrations. The results are shown in FIG. 7 and Table 1. The P20.1 antibody showed the apparent dissociation equilibrium constant (Kd) of about 3.4 nM in respect to the affinity for the P4(20)-Fn. Similarly, a commercially available Flag (DYKDDDDV (SEQ ID NO: 19)) and corresponding antibody M2 were used for examination on the affinity of M2 for Flag-tagged Fn (Flag-Fn). In this case, the Kd value was 2.7 nM.

TABLE 1

|  | $K_a$(1/Ms) | $K_d$(1/s) | $K_D$(M) |
| --- | --- | --- | --- |
| P20.1 Ab | $3.65 \times 10^5$ | $1.23 \times 10^{-3}$ | $3.38 \times 10^{-9}$ |
| FLAG-M2 | $1.46 \times 10^5$ | $3.95 \times 10^{-4}$ | $2.7 \times 10^{-9}$ |

(3-3) Competitive Dissociation by Peptide

For examination on whether an excess of free peptides can disrupt protein-P20.1 antibody binding, at the final washing step of the (3-1) ELISA experiment using the P4(20)-Fn protein, buffer solutions containing different concentrations of the P4(C8) peptide (8-residue peptide PRGYPGQV (SEQ ID NO: 20) synthesized by the Fmoc method) were added to wells and the plates were allowed to stand for 30 minutes.

Figure 8:
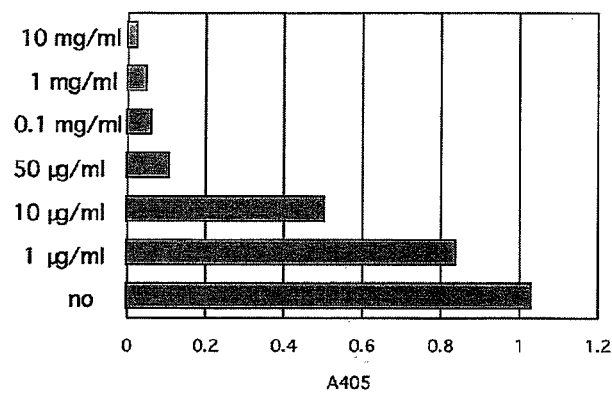
FIG. 8 is the experiment results showing that a partial peptide of the P4(C8) peptide results in competitive dissociation of the P20.1 antibody and the P4(20)-Fn.

From the results shown in FIG. 8, almost complete dissociation was confirmed at the peptide concentration of 0.1 mg/mL.

(3-4) Application of P20.1 Antibody to Western Blotting

Figure 9:
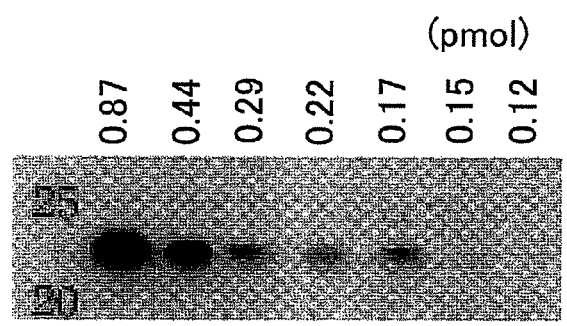

The P4(20)-Fn (0.12 to 0.87 pmol/lane) purified in the (2-1) was separated by SDS electrophoresis, transferred on a PDVF membrane, allowed to react with 1 µg/mL of the P20.1 antibody, and then detected by use of a peroxidase-labeled anti-mouse IgG and a chemiluminescence substrate. The results are shown in FIG. 9. As is clear from FIG. 9, the P20.1 antibody can achieve the detection of the P4 peptide fusion protein of about 0.2 pmol in the western blotting analysis.

Figure 10:
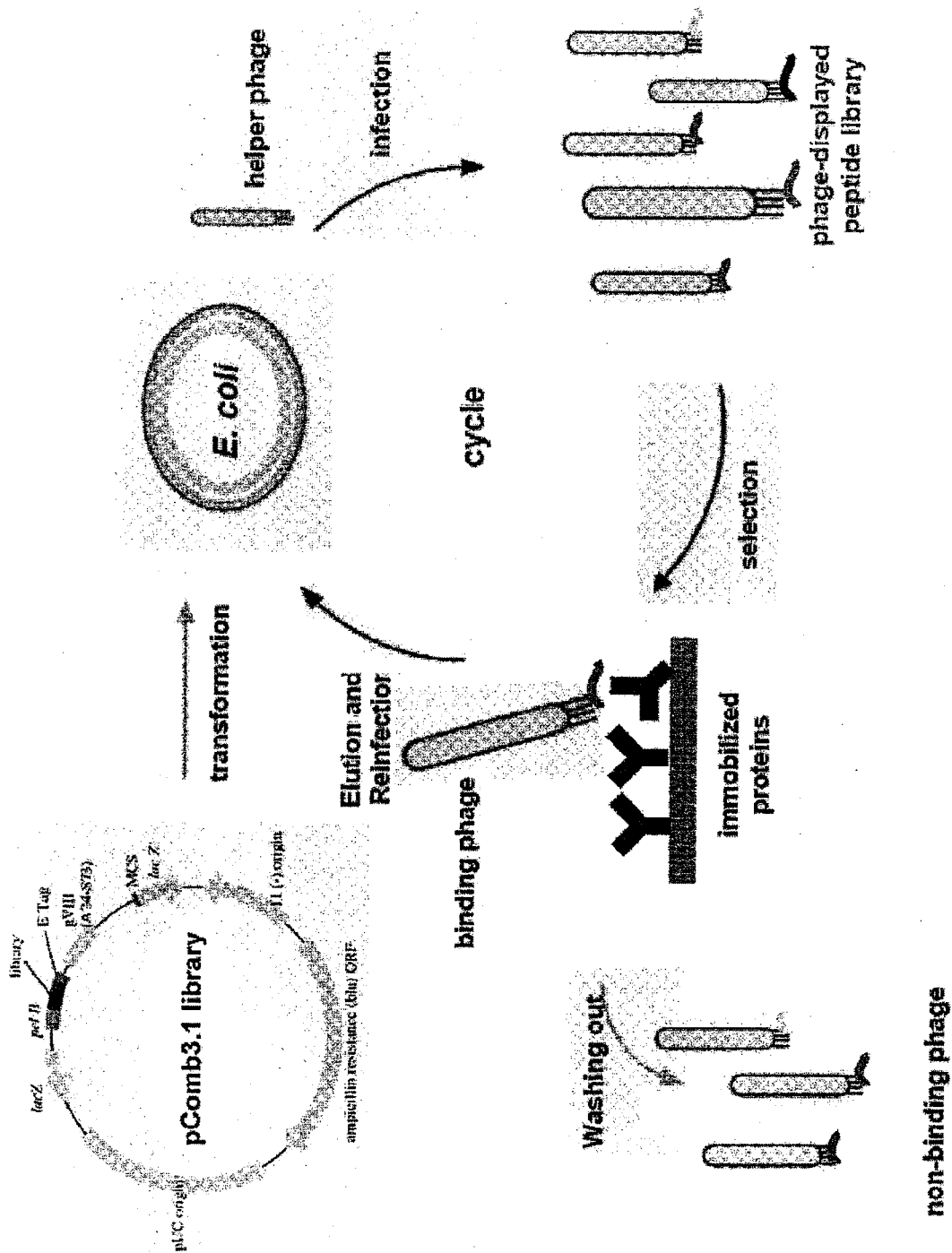

[4] Random Screening of the Peptide Sequence Recognizable by the P20.1 Antibody (4-1) Preparation of Phage Display Library For extensive search for the peptide sequence recognizable by the P20.1 antibody, the phage display method was employed. The outline of the phage display method is shown in FIG. 10. The phagemid shown in FIG. 11 was constructed for insertion of the randomized 7-amino-acid peptide library (all of them have Tyr2 and Gln5 in common) into the N terminus of the gIII coat protein of M13 phage. As a result, the phage library of $10^7$ members was obtained.

(4-2) Selection of P20.1 Antibody-Responsive Clone

Figures 11, 12:
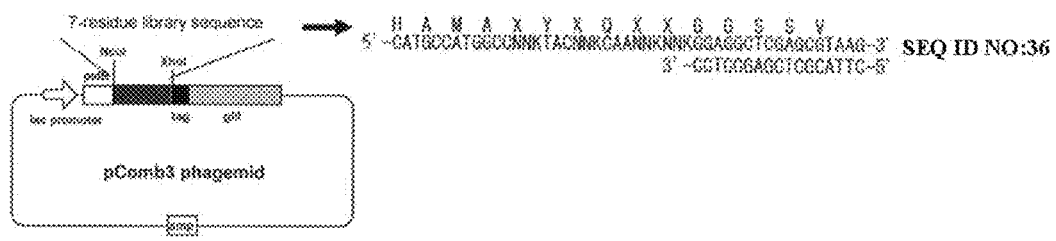

Through panning by use of P20.1 antibody-immobilized magnetic beads, a number of clones bound to the beads were obtained. The sequence of the variable region in these different clones was decoded by DNA sequencing, and the sequence pattern as shown in FIG. 12 was obtained. The results showed that recognition of peptides by the P20.1 antibody requires the presence of tyrosine, glycine and glutamine at position 2, 4 and 5 from the N terminus of peptides, respectively (Tyr2, Gly4, Gln5), and in addition that the P20.1 antibody shows high selectivity to the proline at position 3 (Pro3) from the N terminus of peptides. It was also found that the P20.1 antibody accepts a hydrophobic amino acid at position 6, and has no particularly strong selectivity to an amino acid residue at position 1 or 7. Namely, it can be said that the P20.1 antibody generally has a high affinity for the following peptide sequence:

X1-Tyr2-Pro3-Gly4-Gln5-X6: SEQ ID NO:21

(wherein X1 is any amino acid residue; Pro3 may be an amino acid having a small side chain, such as S, V, C, A, T, E, G and D; and X6 is any hydrophobic amino acid).

[5] X-Ray Crystallography of the P20.1 Antibody Fab Fragment-Peptide Complex (5-1) Amino Acid Sequencing of the P20.1 Antibody Variable Region DNA Cloning from Hybridoma The structure determination of the P20.1 antibody Fab fragment requires its exact amino acid sequence. For sequence determination, the total RNA was extracted from the mouse-mouse hybridoma P20.1 (FERN BP-11061) by use of Total RNA Isolation System (Promega). The volume and concentration of the extracted total RNA were 100 µL and 22.7 ng/µL, respectively. Using this RNA as a template, RT-PCR was performed with Mouse Ig-Primer Set (Novagen). The amplified PCR product was ligated to the pDrive Cloning Vector (QIAGEN PCR Cloning Kit), which was then used for transformation of *Escherichia coli* DH5a. The transformants were cultured on LB plates supplemented with ampicillin, X-gal and IPTG, to form colonies.

In respect to the obtained DNA clone of the P20.1 antibody Fab fragment, the DNA sequencing of the variable region was performed using the primers for RT-PCR described above. Based on the determined sequence, internal primers were designed and then used for sequencing of the constant region in succession. The obtained DNA/amino acid sequences are shown in the SEQ ID NOS: 3 and 5 of the appended sequence list, as well as FIGS. 13 and 14. SEQ ID NO: 3 and FIG. 13 show the DNA/amino acid sequences of the heavy chain variable region of the P20.1 antibody Fab fragment. SEQ ID NO: 5 and FIG. 14 show the DNA/amino acid sequences of the light chain variable region thereof.

(5-2) Complex Crystallization

28 µL of the P20.1 antibody Fab fragment (10 mg/mL in 5 mM Tris, 50 mM NaCl, pH 7.4), which was prepared in the (1-3), and 4 µL of a P4(C8) peptide solution (10 mg/mL) were mixed and then the mixture was allowed to stand overnight. Crystallization was performed under 96 conditions in total by the hanging drop method using a Wizard I and II kit (Emerald Biostructures). As a result, a pillar-shaped crystal was observed under the conditions of 100 mM acetate buffer solution (pH 4.5) containing 20% (w/v) of PEG3000. Then, examination was made at various concentrations around 20% of PEG3000, and finally the concentration of PEG was optimized at 23%. The obtained protein crystal is shown in FIG. 15. In FIG. 15, the inside of the left circle is a schematic view showing the crystallized complex of the P20.1 antibody Fab fragment and the P4(C8) peptide, and the right image is an enlarged view of the crystallized complex.

(5-3) Structure Determination

X-ray crystallography of the crystal obtained in the (5-2) was conducted at a resolution of 1.8 Å using Beamline BL-44XU of the Synchrotron Radiation Facility SPring-8. The statistics are shown in Table 2.

TABLE 2

| Experimental conditions | |
|---|---|
| Beamline | SPring-8/BL-44XU (Institute for Protein Research) |
| Wavelength | 0.9000 Å |
| Exposure time/frame | 3.0 sec. |
| Oscillation angle/frame | 1.5 deg. |
| No. of frames | 150* |
| Total oscillation range | 225 deg. |
| Crystal data | |
| Crystal system & Spacegroup | triclinic, P1 |
| Unit cell dimensions | a = 40.05 Å, b = 65.27 Å, c = 85.03 Å |
| | α = 99.93 deg., β = 93.50 deg., γ = 96.46 deg. |

TABLE 2-continued

Molecules present in the asymmetric unit (Fab + C8 peptide) × 2
Data colletion statistics

| | |
|---|---|
| Resolution range (Å) | 100.0-1.80 (1.86-1.80) |
| Total No. of reflections | 187,728 |
| No. of unique reflections | 73,337 |
| Data completeness (%) | 97.9 (96.8) |
| I > 2σ(I) | 84.4 (57.6) |
| Data redundancy | 2.5 (2.5) |
| $R_{merge}$ (%) | 4.0 (24.8) |
| <I/σ(I)> (signal-to-noise ratio) | 16.0 (4.0) |

Based on the obtained data, the 3D structure of the above complex was determined by the molecular replacement method. As a template for the molecular replacement method, the Monoclonal Antibody 2D12.5 Fab Complexed with Gd-DOTA (PDB ID: 1NC4) was used. (Like the P20.1 antibody, the antibody 2D12.5 is an IgG1 isotype and has λ light chains.) As a result, the structure of two Fab molecules in a unit cell was determined.

The primary structure of the P20.1 antibody determined in the (5-1) was used for phase improvement and structure refinement. Automated modeling was performed by ARP/wARP using this primary structure data and the molecular replacement solutions. As a result, the model for 736 residues of 884 residues was built, and the structures of the side chains of 650 residues of them were also assigned to the model. Based on the improved map, model fitting was performed for structure refinement. The statistics are shown in Table 3.

TABLE 3

| Refinement statistics | |
|---|---|
| Resolution limit | 83.3-1.80 |
| $R_{work}$ | 18.6 |
| $R_{free}$ | 21.2 |
| Non-H atoms | 6819 |
| Fab (No. residues) | 6357 (832) |
| C8 peptide (No. residues) | 88 (16) |
| Water | 362 |
| Glycerol | 12 |
| R.m.s.d from ideal values | |
| Bond lengths (Å) | 0.008 |
| Bond angles (deg) | 1.19 |
| Mean B-factor for protein atoms; | (Main-chain/Side-chain) (Å2) |
| H-chain-1 | 22.34/23.34 |
| L-chain-1 | 18.83/20.74 |
| Peptide-1 | 26.37/25.41 |
| H-chain-2 | 28.66/29.31 |
| L-chain-2 | 26.87/28.17 |
| Peptide-2 | 30.77/29.94 |
| Ramachandran plot (%) | |
| Most favored | 92.3 |
| Additionally allowed | 6.9 |
| Generously allowed | 0.6 |
| Disallowed | 0.3 (L-chain, Thr-53) |

Figure 16:
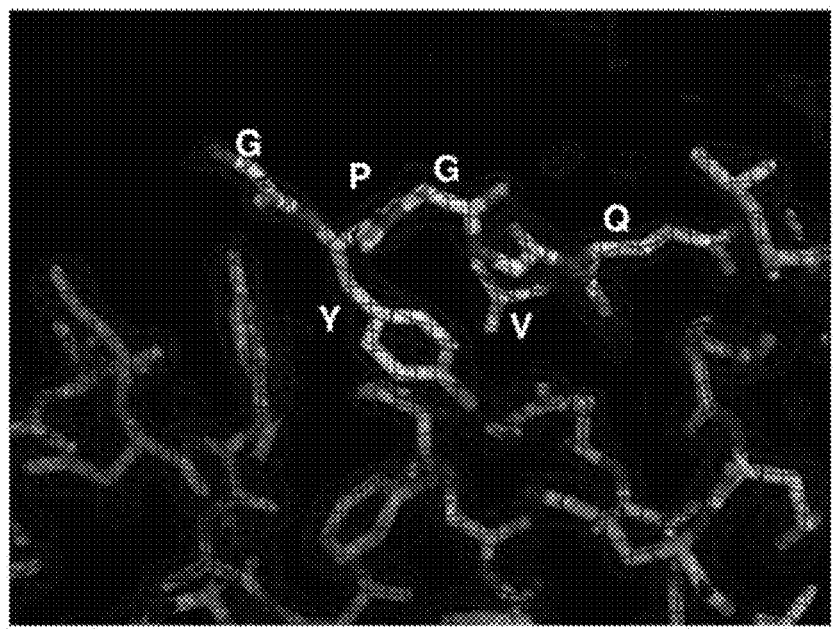

Observation on the electron density revealed that the peptide binds to each of the two Fab molecules in an asymmetric unit. In each case, a reliable model was able to be built in the region corresponding to the C-terminal GYPGQV (P4 sequence, SEQ ID NO: 1) of the P4(C8) peptide. FIG. 16 is an enlarged view showing the entire structure and antigen recognition site of one of the two complexes. The determined 3D structure significantly clarified the reason of the specificity of the peptide recognition sequence (i.e., Tyr2, Gly4 and Gln5 are indispensable for recognition).

From the viewpoint of structural chemistry, the basic structure for recognition of the peptide antigen (the tag peptide of the present invention) by the antibody of the present invention was determined according to atomic coordinates. As a result, the following (A) and (B) are made possible by use of protein engineering methods.
(A) providing the antibody with an additional property without affecting its own recognition ability
(B) changing specificity and/or affinity into more desirable ones In particular, specific labeling can be achieved by modification of amino acid residues that are not responsible for tag recognition; and an additional complementary region is introduced into the antibody and the peptide by modification of amino acid residues at sites other than the core region for recognition and thereby antibodies that have a stronger binding capacity or can bind preferentially to a certain long peptide can be created.

[6] Preparation of P20.1 Antibody-Derived scFv
(6-1) Construct Preparation, Expression and Purification In order that the P20.1 antibody derived from the mouse-mouse hybridoma P20.1 (FERM BP-11061) is used not only as an antibody, but also as a reagent that can be recombinantly expressed and purified in a simple manner, the single chain Fv fragment (scFv) of the P20.1 antibody was prepared. The expression construct shown in SEQ ID NO: 7 and FIG. 17 was prepared by use of the amino acid sequence of the P20.1 antibody variable region identified in the (5-1), and scFv expression was achieved by use of the pET11c vector and *Escherichia coli* BL21. The scFv, which was obtained as an inclusion body, was solubilized from insoluble fractions with guanidine hydrochloride, purified with Ni-NTA resin and refolded by sequential dialysis. As a result, about 2 mg of the scFv was obtained from 1 L of the culture medium.

Figure 19A:
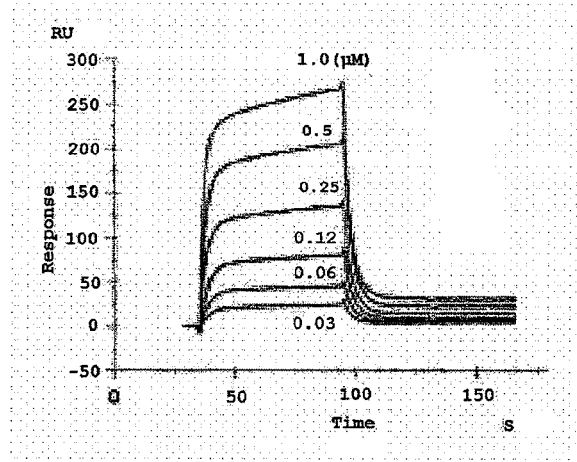
Figure 19B:
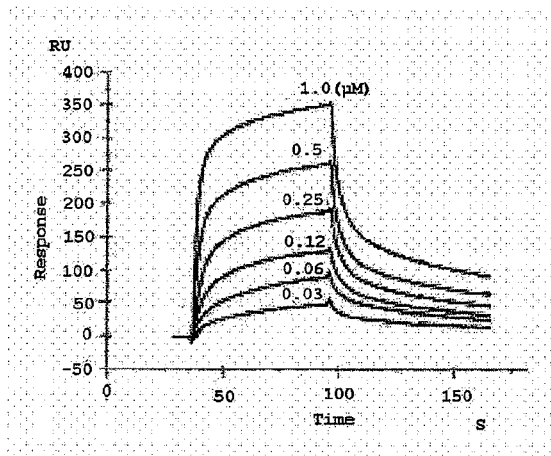
Figure 19C:
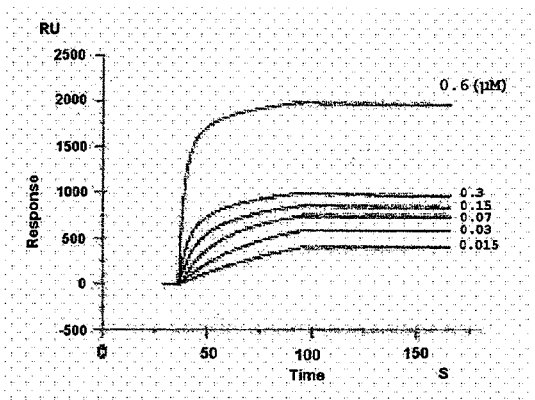

The binding strength of the scFv is weak because of the monovalence. For this reason, a recombinant protein fused with streptavidin downstream of the scFv was prepared for substantial improvement in affinity. This utilizes the property of streptavidin, i.e., tetramerization. Protein expression and purification were performed in the same manner as in the case of the scFv except for using the construct shown in FIG. 18, to give a scFv tetramer (tetra-scFv).
(6-2) Activity of scFv The prepared scFv and tetra-scFv antibodies were examined for their peptide binding capacity with Biacore using a P4(20)-Fn-immobilized sensor chip. For comparison, the Fab fragment was used for the same examination as above. The results of the Fab fragment, scFv antibody and tetra-scFv antibody are shown in FIGS. 19 (*a*), (*b*) and (*c*), respectively. As is clear from FIGS. 19 (*a*), (*b*) and (*c*), the scFv antibody showed almost the same binding activity as that of the Fab fragment and no decline in antigen binding capacity despite of a single chain. In addition, the tetra-scFv antibody hardly dissociated and showed a strong binding capacity far beyond that of the original IgG molecule (P20.1 antibody).

Figure 20A:
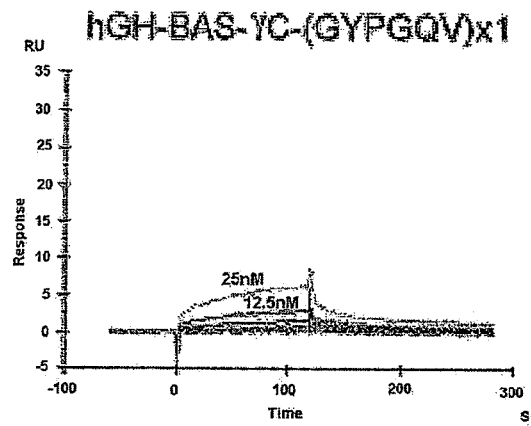
Figure 20B:
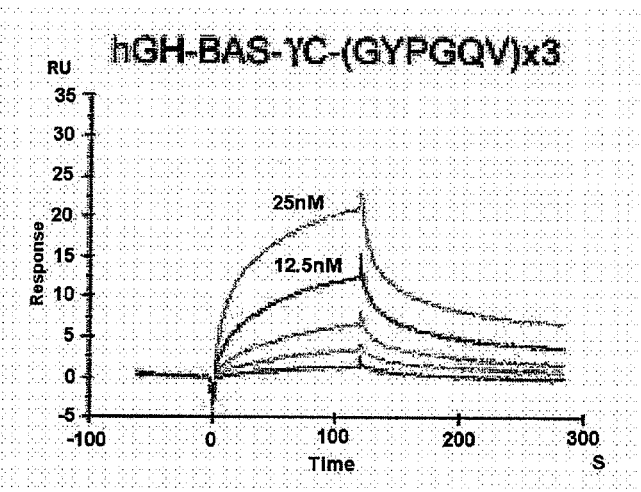
Figure 20C:
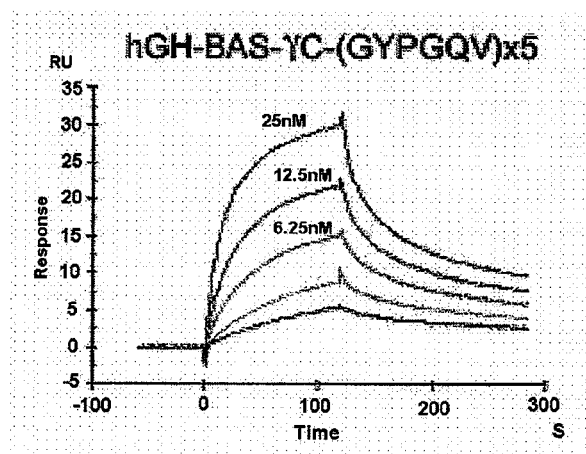

[7] Effects of P4 Sequence (GYPGQV (SEQ ID NO: 1)) Repeat on Improvement in the Efficacious Affinity for the P20.1 Antibody (7-1) Kinetics Analysis Based on Surface Plasmon Resonance For improvement of the efficacious affinity for the P20.1 antibody, tag peptide fusion proteins having a repeated sequence, specifically 1, 3 or 5 repeats of the P4 sequence (referred to as P4×1, P4×3 or P4×5, in the above order) were prepared (see the above (2-2)). These proteins were allowed to separately pass at a flow rate of 20 µL/min over the P20.1 antibody-immobilized sensor chip, and kinetics analysis was conducted using Biacore X-100 (GE Healthcare). The results of the tagged fusion protein having 1 repeat of the P4 sequence are shown in FIG. 20 (a). The results of the tagged fusion protein having 3 repeats of the P4 sequence are shown in FIG. 20 (b). The results of the tagged fusion protein having 5 repeats of the P4 sequence are shown in FIG. 20 (c). As a result, the tagged fusion protein having only one repeat of the P4 sequence (FIG. 20 (a)) showed an extremely weak affinity for the P20.1 antibody, while each of the tagged fusion proteins having multiple repeats of the P4 sequence showed a 4-fold or more strength in terms of the maximum binding capacity. Compared with the P4×3 tag (FIG. 20 (b)), the P4×5 tag (FIG. 20 (c)) showed a further increased binding capacity, and this result makes it clear that such an increased effect depends on the repeat number of the P4 sequence (6 residues).

Figure 21:
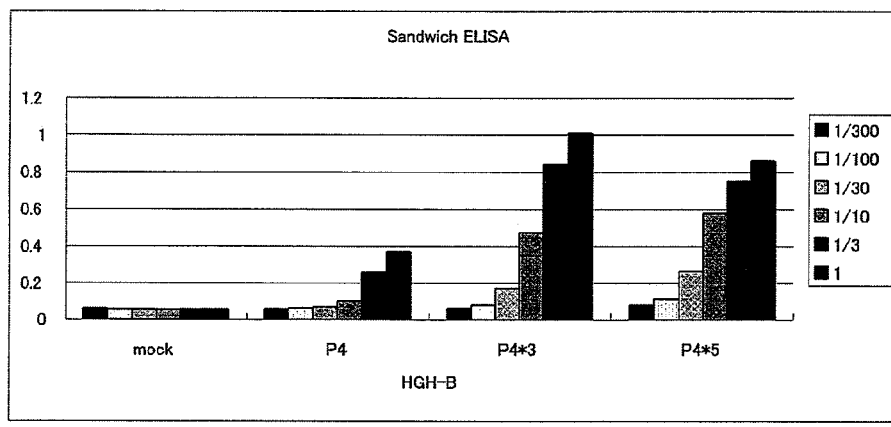

(7-2) Establishment of Sandwich ELISA System 7-2-1: Case where the P20.1 Antibody is Used as a Detection Antibody The anti-hGH monoclonal antibody HGH-B was immobilized to microtiter plates. After blocking, the supernatant of cells transiently expressing the hGH-γC-P4 fusion protein having P4×1, P4×3 or P4×5 linked thereto (see FIG. 3, FIG. 4 and SEQ ID NO: 15) was added at various dilution ratios to wells of the plates, which were then allowed to stand at 4° C. overnight. In this way, such a fusion protein was captured by the antibody on the plates. After washing, a biotinylated P20.1 antibody (5 µg/mL) was allowed to react with the fusion protein at room temperature for 30 minutes. After 3-time washing, peroxidase-labeled streptavidin (Zymed) was added to the plates, which were then allowed to stand at room temperature for additional 15 minutes. After addition of peroxidase substrate (ABTS), the absorbance at 405 nm was measured. The results are shown in FIG. 21. As shown in FIG. 21, only weak signals were detected in 3-fold or less diluted supernatant in the case of the protein fused with only one repeat of the P4 sequence (6 amino acids), while in the case of the protein fused with the repeated sequence P4×3 (18 amino acids) or P4×5 (30 amino acids), dose-dependent signals were observed in 30-fold or less diluted supernatant.

7-2-2: Case where the P20.1 Antibody is Used as a Capture Antibody

Figure 22:
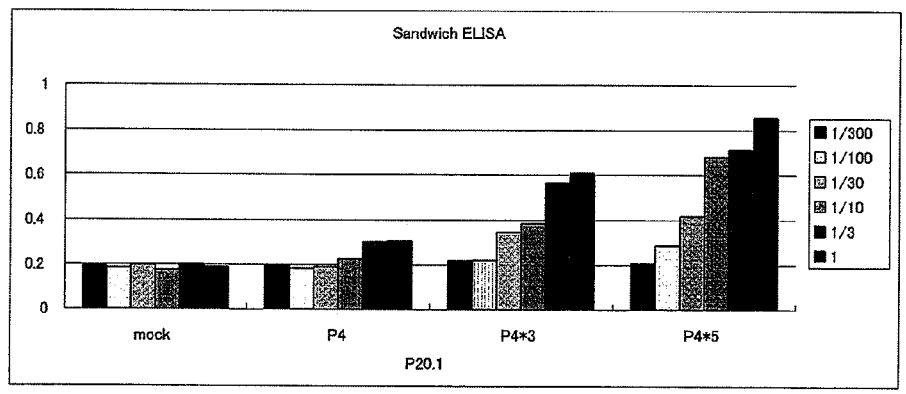

The P20.1 antibody was immobilized to microtiter plates at 10 µg/mL, and after blocking, the hGH-γC-P4 fusion protein was captured in the same manner as in the (7-2-1). For detection, a rabbit antiserum (1:100 dilution) against the BAS sequence and the peroxidase-labeled anti-rabbit IgG, which was used as a secondary antibody, were used. The results are shown in FIG. 22. In this case as well, tagged proteins having multiple repeats of the P4 sequence provide the ELISA system with a sufficient detection sensitivity as shown in FIG. 22.

(7-3) Pull-Down Efficiency of The Tag Peptide Fusion Protein Using P20.1 Antibody-Immobilized Beads Three different hGH-γC-P4 fusion proteins, which have P4×1, P4×3 or P4×5, were separately expressed in HEK293T cells. The fusion protein in the separate cell culture supernatant was quantified by the sandwich ELISA (which adopts a system of hGH antibody-mediated capture+anti-BAS serum-mediated detection, and is not dependent on the responsiveness to the P20.1 antibody) (before pull-down). Aside from this, to 1 mL of the cell culture supernatant, 20 µL of the P20.1 antibody-Sepharose (bead form) was added, and then the mixture was allowed to react at 4° C. for 1 hour. After the beads were precipitated by centrifugation, the fusion protein in the supernatant was quantified by the sandwich ELISA (which adopts a system of hGH antibody-mediated capture+ anti-BAS serum-mediated detection, and is not dependent on the responsiveness to the P20.1 antibody) (after pull-down). The fusion protein purified with Ni-NTA agarose was used as a standard, and based on the standard curve, the fusion protein concentrations before and after pull-down by the P20.1 antibody were determined. The results are shown in Table 4. As is clear from Table 4, 3 to 5 repeats of the P4 sequence achieves the binding efficiency of about 80%.

TABLE 4

| | Fusion protein (µg/mL) | | |
|---|---|---|---|
| Tag sequence | Before pull-down | After pull-down | Binding efficiency |
| P4 | 0.7 | 0.6 | 14% |
| P4 × 3 | 0.98 | 0.22 | 78% |
| P4 × 5 | 0.85 | 0.17 | 80% |

[8] Purification of Protein Tagged with P4 Repeats Using P20.1 Antibody-Immobilized Beads (8-1) Elution Conditions With 8 mL of the culture supernatant of cells expressing the P4×3-tagged hGH fusion protein, 100 µL of the P20.1 antibody-Sepharose (0.2 mg in terms of the P20.1 antibody, bead form) was mixed, and then the mixture was allowed to react at 4° C. for 3 hours. After the reaction, the beads were washed with 3 mL of Tris-buffered saline (TBS; 20 mM Tris-HCl, 150 mM NaCl, pH 7.5), and 300 µL of an eluent as shown below was added to and mixed with the beads at room temperature for 10 minutes. The effluent obtained by each eluent was concentrated and then was subjected to SDS gel electrophoresis at an equal amount. For comparison, affinity binding was also performed using Ni-NTA beads on the same conditions as above, and the effluent obtained by use of imidazole as an eluent was analyzed simultaneously.

Figure 23A:
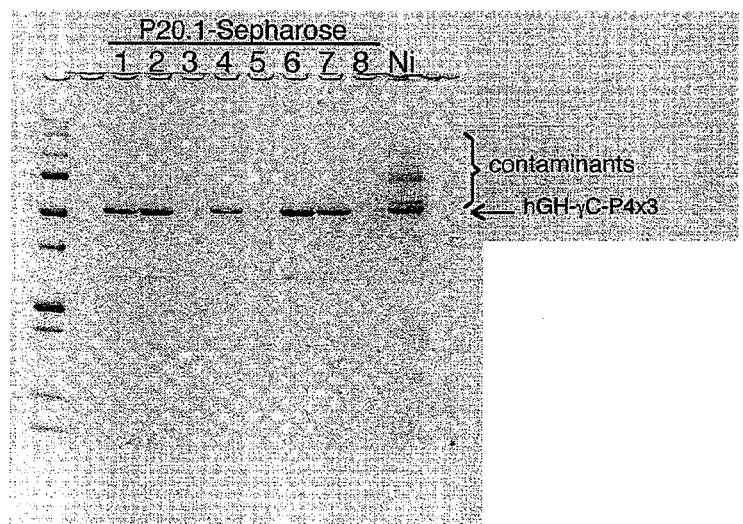

Number-Eluent
(1) 0.1 mg/mL P4(C8) peptide in TBS
(2) 1 mg/mL P4(C8) peptide in TBS
(3) 0.1 M glycine-hydrochloric acid, pH 2.2
(4) 50 mM triethanolamine (in TBS), pH 11.5
(5) 2 M potassium iodide (in TBS)
(6) 40% (v/v) propylene glycol+1 M sodium chloride in TBS
(7) 40% (v/v) propylene glycol+1 M potassium iodide in TBS
(8) TBS The results are shown in FIG. 23 (a). The above-mentioned numbers correspond to the lane numbers in FIG. 23 (a). "Ni" indicates the effluent from Ni-NTA beads. As shown in FIG. 23 (a), the tagged fusion protein which was bound to the P20.1 antibody-Sepharose was not only eluted with 0.1 mg/mL or more of the P4(C8) peptide, but also completely eluted by combined use of propylene glycol and sodium chloride. On the other hand, the tagged fusion protein was not eluted at all under some elution conditions often adopted in monoclonal antibody-based affinity chromatography (pH 2.2 acid conditions, chaotropic ions such as high-concentration iodide ion), and was only partially eluted under basic conditions of pH 11.5. The results showed that the tag peptide fusion protein was eluted under mild conditions. Compared with the effluent from Ni-NTA beads (Ni in the rightmost lane), each effluent from P20.1 antibody beads contained no impurities, and this result proved that an extremely highly purified product can be obtained in a single step.

The same experiments were conducted using the following eluents.

Number-Eluent
(1) TBS
(2) 0.5 mg/mL P4(C8) peptide in TBS
(3) 20% (v/v) propylene glycol in TBS
(4) 30% (v/v) propylene glycol in TBS
(5) 40% (v/v) propylene glycol in TBS
(6) 60% (v/v) propylene glycol in TBS
(7) 40% (v/v) ethylene glycol in TBS
(8) 40% (v/v) DMSO in TBS The results are shown in FIG. 23 (b). The above-mentioned numbers correspond to the lane numbers in FIG. 23 (b). It is evident from the results shown in FIG. 23 (b) that a preferable concentration of propylene glycol is 40% or more, and that a high concentration of NaCl is not needed.

(8-2) Purification of Recombinant F-Spondin Protein in Crystallization Quality

F-spondin, which is a protein responsible for the axon guidance in the brain during the fetal period, was fused with the tag sequence P4×3, and the resulting fusion protein was purified with the P20.1 antibody-Sepharose. In the expression construct for this fusion protein, the P4×3 sequence (18 residues) is attached to the downstream of the signal sequence of mouse nidogen, and further fused with the N-terminal 146-amino-acid domain of F-spondin via the TEV protease cleavage sequence (7 residues). The base sequence at positions 901 to 1560 in the 6045-base DNA encoding the prepared recombinant F-spondin protein is shown in SEQ ID NO: 16 and FIG. 24. In SEQ ID NO: 16 and FIG. 24, the base sequence at nucleotide positions 1 to 900 and 1561 to 6045 is omitted. The amino acid sequence of the recombinant protein encoded by the DNA sequence of SEQ ID NO: 16 is shown in SEQ ID NOS: 16 and 17 and FIG. 24. The DNA sequence encoding F-spondin is described in, for example, Miyamoto et al. Arch. Biochem. Biophys. 390 (1), 93-100, 2001.

Figure 25:
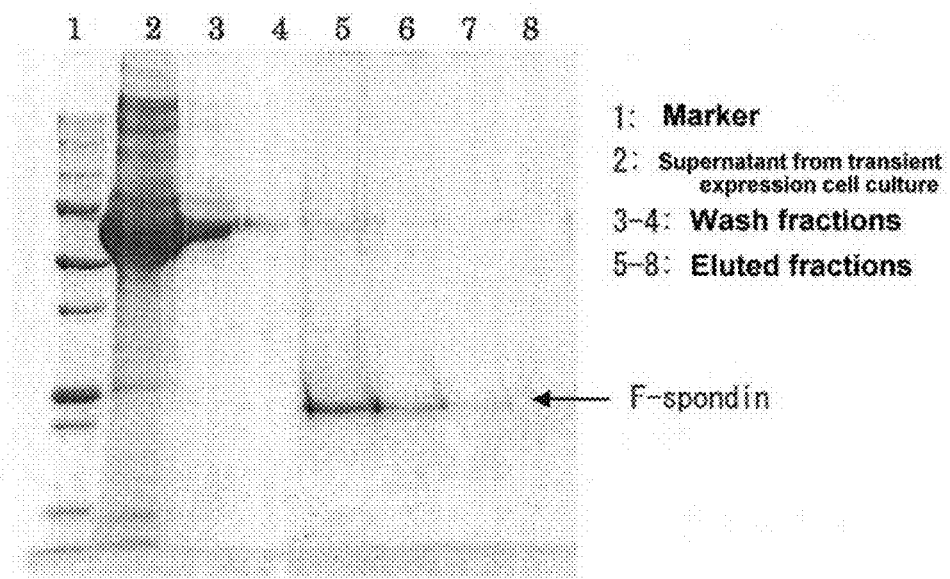

The tag peptide/F-spondin fusion protein was transiently expressed in HEK293T cells by use of the above-mentioned construct, and 400 mL of the culture supernatant was collected one week later. This supernatant was allowed to adsorb onto 2 mL of the P20.1 antibody-Sepharose. Washing with TBS and eluting with a buffer solution containing 40% propylene glycol and 1 M NaCl were performed, and the resulting effluent was subjected to SDS gel electrophoresis. The results are shown in FIG. 25. In FIG. 25, the lanes are as follows: lane 1: marker, lane 2: supernatant from transient expression cell culture, lanes 3 and 4: wash fractions, lanes 5 to 8: eluted fractions. As is clear from FIG. 25, only the tag peptide/F-spondin fusion protein was specifically eluted with a buffer solution containing 40% propylene glycol and 1 M NaCl after adsorption onto the P20.1 antibody-Sepharose.

Figure 26:
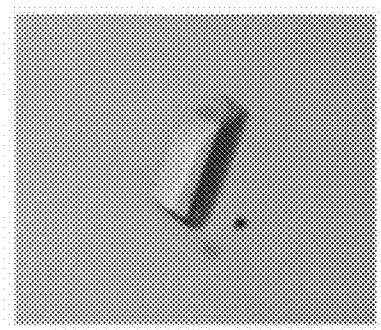
Figure 27:
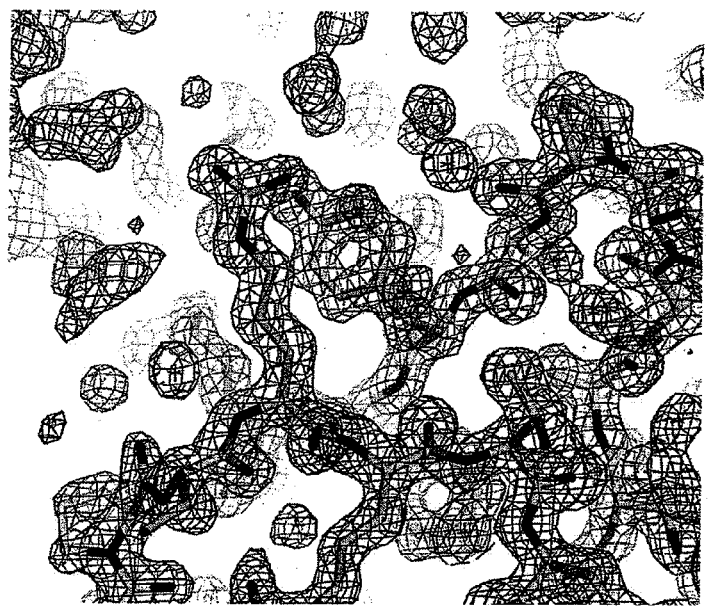

The purified F-spondin protein was concentrated and then subjected to crystallization screening. As a result, a good-quality single crystal was obtained under conditions using 0.1 M Tris (pH 8.5), 0.2 M trimethylamine n-oxide dihydrate and 20% PEG2000. An enlarged image of the crystal of the purified F-spondin is shown in FIG. 26. The X ray crystal diffraction analysis of this crystal was conducted by Beamline AR-NW12A of High Energy Accelerator Research Organization and data at 1.85 Å resolution were obtained. As shown in FIG. 27, an extremely clear electron density map was obtained and the model building, which usually takes one day to several weeks, was completed in only 1 hour. As a result, the 3D structure of the N-terminal domain of F-spondin became clear although unidentified until then. In addition, it was proved that the high-quality protein purification system by combined use of the P20.1 antibody and P4×3 tag is extremely excellent.

(8-3) Purification of Large Protein Reelin

Figure 28:
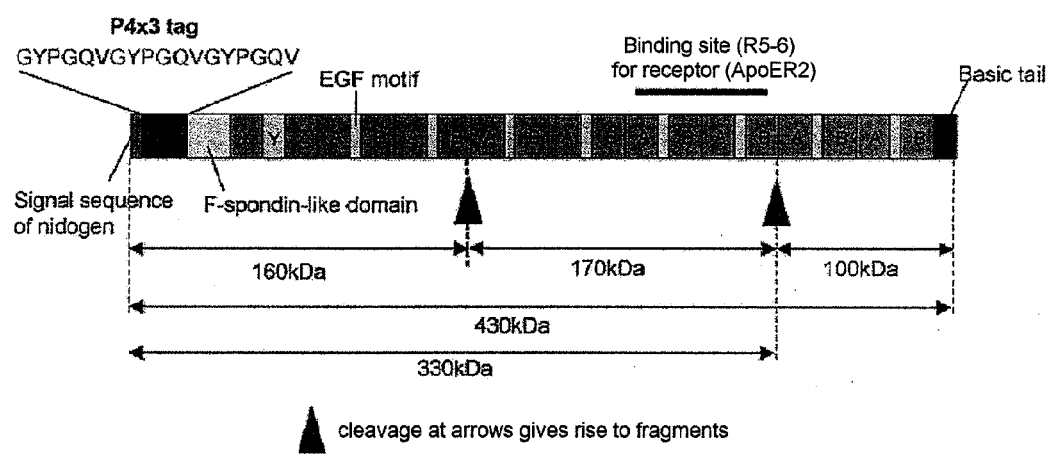

Reelin is a huge extracellular protein with a molecular weight of 400 kDa or more and essential for development of the mammalian brain. No one in the world has succeeded in its purification due to its size and instability. An expression construct for a fusion protein having the P4×3 tag attached to the N-terminus of reelin was prepared. This expression construct is shown in FIG. 28.

Figure 29:
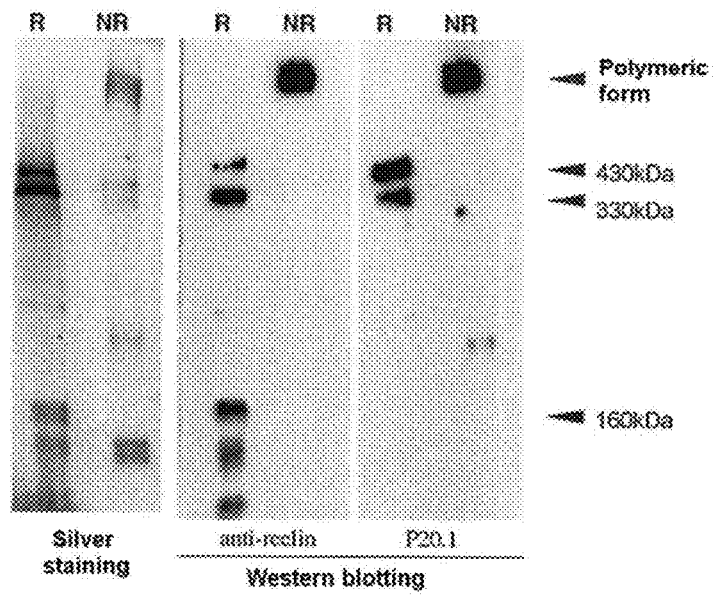

The tag peptide/reelin fusion protein was transiently expressed in HEK293T cells by use of the construct shown in FIG. 28 and 800 mL of the culture supernatant was collected one week later. The fusion protein was purified using the P20.1 antibody-Sepharose in the same manner as in the case of F-spondin, and finally about 30 µg of the fusion protein was obtained. The results of SDS gel electrophoresis and western blotting of the obtained protein are shown in FIG. 29. In FIG. 29, R and NR represent reducing conditions and non-reducing conditions, respectively. As is clear from FIG. 29, in SDS gel electrophoresis, the fusion protein was in a huge polymeric form with a molecular weight of 10 million or more under non-reducing conditions, while the main bands of 430 kDa and 330 kDa and some bands corresponding to 170 kDa or less fragments were observed under reducing conditions. The results of western blotting using an anti-reelin antibody and the P20.1 antibody showed that all these bands correspond to full length reelin or its partially degraded fragments, and that the recombinant reelin protein can be obtained with 95% or more purity in a single step.

[9] Effect of the Tag Sequence Having Repeats of the 4-Residue YPGQ (SEQ ID NO: 18)

(9-1) Preparation of Tag Peptide/Fibronectin Fusion Protein

Figure 30:
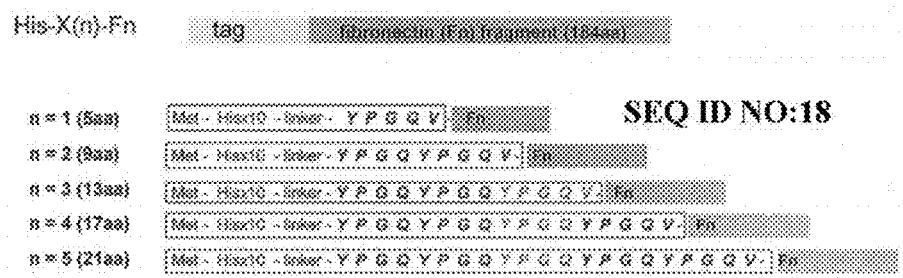
Figure 31:
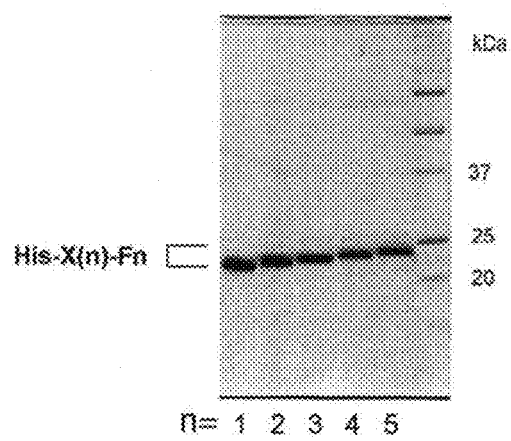

Tag peptide/fibronectin fusion proteins, which have the tag sequence having repeats of the 4-residue YPGQ (SEQ ID NO: 18), which is the minimum recognition unit for the P20.1 antibody, were prepared. Specifically, as shown in FIG. 30, the construct for each fusion protein was named His-X(n)-Fn (wherein n is the repeat number), and 5 different constructs with 1 to 5 repeats were prepared. *Escherichia coli* BL21 (DE3) cells were transformed with these respective constructs described above, and induced expression of the corresponding tag peptide fusion proteins was achieved by a usual method. Each of the produced tag peptide/fibronectin fusion proteins was purified using Ni-NTA agarose. The electrophoresis image of the purified proteins is shown in FIG. 31.

(9-2) Kinetics Analysis Based on Surface Plasmon Resonance

Figure 32:
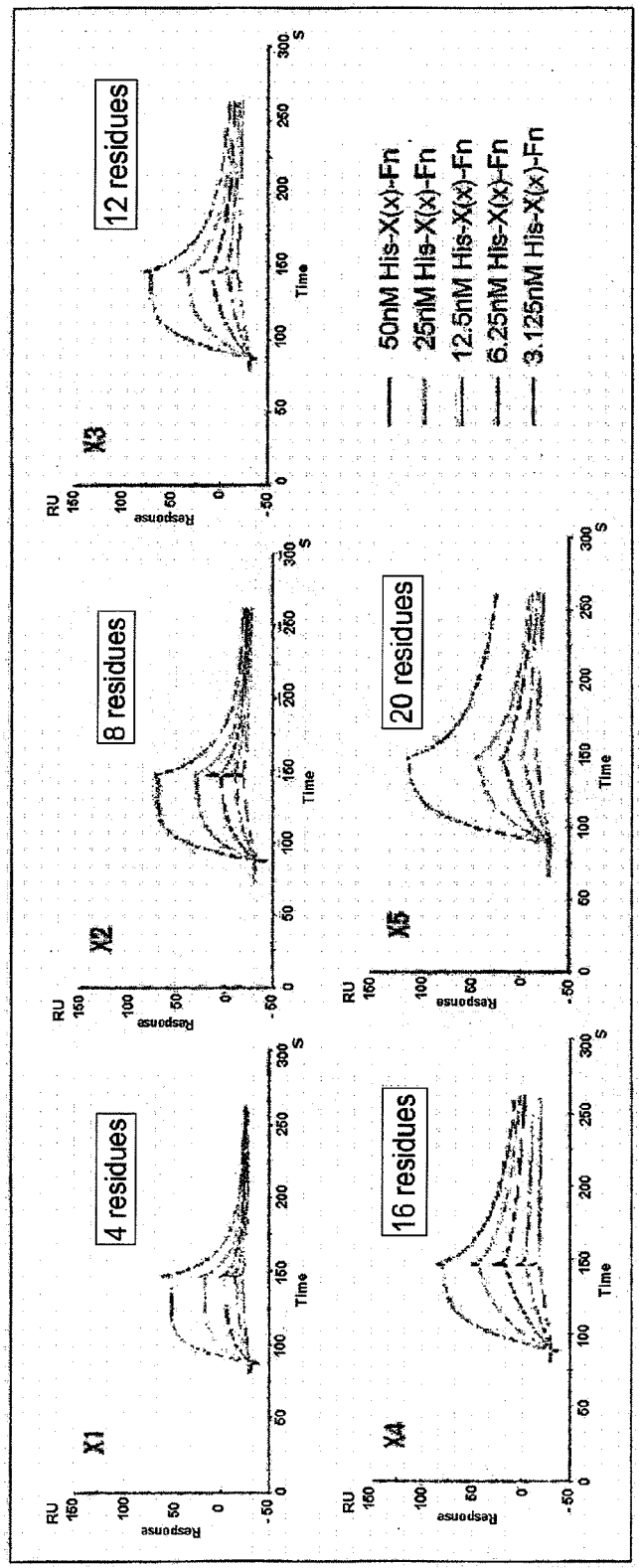

The tag peptide/fibronectin fusion proteins obtained in the (9-1), which have a repeated sequence, specifically 1, 2, 3, 4 or 5 repeats of the 4-residue sequence YPGQ (SEQ ID NO: 18) (referred to as X(1), X(2), X(3), X(4) or X(5)) were allowed to separately pass at a flow rate of 20 µL/min over the P20.1 antibody-immobilized sensor chip, and kinetics analysis was conducted using Biacore 2000 (GE Healthcare). The results are shown in FIG. 32. As shown in FIG. 32, the repeat of the 4-residue sequence provides an increased binding capacity like the repeat of the P4 sequence (6 residues) described before. It was proved that particularly, the X(5) tag having 5 repeats provides a higher affinity (Kd=10 nM) than that of the P4×3 tag.

Figures 33, 34:
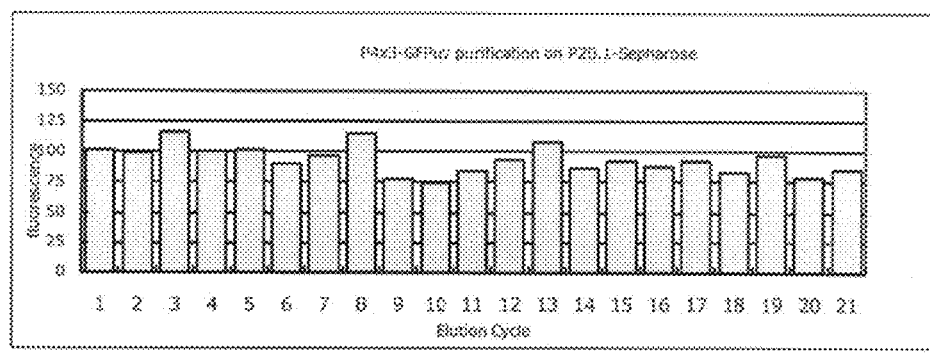

[10] Effects of the Repeated Use of P20.1 Antibody-Sepharose (10-1) Preparation of Tag Peptide/GFPuv Fusion Protein An expression construct for a tag peptide/GFPuv fusion protein, which has the tag sequence P4×3 attached to the N-terminus of a fluorescence protein GFPuv, was prepared (see FIG. 33). The insert was prepared by extension PCR and then was inserted into the NcoI-BamHI site of the expression vector pET16b (Novagen). *Escherichia coli* BL21 (DE3) cells were transformed with this construct, induced expression of the corresponding tag peptide fusion protein was achieved by a usual method and *Escherichia coli* lysate was prepared.

(10-2) Repeated Purification of the Tag Peptide/GFPuv Fusion Protein Using P20.1 Antibody-Sepharose 0.25 mL of the *Escherichia coli* lysate containing the tag peptide/GFPuv fusion protein prepared in the (10-1) was applied to 0.5 mL of the P20.1 antibody-Sepharose. After this, the P20.1 antibody-Sepharose was allowed to stand at 4° C. for 20 minutes and washed with 2 mL of Tris-buffered saline (TBS; 20 mM Tris-HCl, 150 mM NaCl, pH 7.5). Then, eluting with 2.5 mL of an eluent (40% (v/v) propylene glycol/TBS) and washing with 5 mL of TBS were performed. This purification cycle was performed 21 times. The amount of GFPuv in each eluted fraction was determined based on fluorescence readings at 390 nm (excitation wavelength)/510 nm (fluorescence wavelength).

The results are shown in FIG. 34. As is clear from FIG. 34, the amount of the tag peptide/GFPuv fusion protein, which was bound and eluted in each cycle, was almost constant through the 21 cycles of elution/regeneration, and its yield after 21 cycles declined by only about 10% at the maximum. These results showed that the system of the present invention using elution with propylene glycol is extremely economical because the system can be used multiple times/over a long period of time, compared with commercially available systems which require regeneration of resin after an elution step due to some kind of denaturating conditions.

The present invention is not limited to the aforementioned embodiments and examples, and various modifications can be made within the scope of the appended claims. Other embodiments provided by suitably combining different technical means disclosed in the respective embodiments of the present invention are also within the technical scope of the present invention. All the academic publications and patent literatures cited in the above description are incorporated herein by reference.

INDUSTRIAL APPLICABILITY

According to the present invention, the tag peptide, the tag peptide fusion protein and the antibody against the tag peptide are useful for a system that enables recombinant proteins to be highly purified in an easy and inexpensive manner. According to the present invention, the purification method for proteins is useful as a method that enables recombinant proteins to be highly purified in an easy and inexpensive manner. According to the present invention, the detection or quantification method for proteins is useful as a method that enables recombinant proteins to be efficiently detected or quantified.

The invention claimed is:

1. An isolated tag peptide selected from one of the following (1) or (2):
   (1) an isolated tag peptide consisting of the amino acid sequence represented by (Tyr-X$_2$-Gly-Gln: SEQ ID NO:96)m, wherein X$_2$ represents Pro, Ser, Val, Ala, Thr, or Asp, amino acid residues 2-5 of SEQ ID NOs:46, 47, 58, 67, 86 or 88 and m represents an integer of 3 to 5; or
   (2) an isolated tag peptide consisting of the above (1) and one hydrophobic amino acid added to the C-terminus thereof.

2. The isolated tag peptide according to claim 1, wherein the hydrophobic amino acid is Val.

3. The isolated tag peptide according to claim 1, which consists of the amino acid sequence represented by any of the following (a) to (f):
   (a) SEQ ID NO:37;
   (b) SEQ ID NO:38;
   (c) SEQ ID NO:39;
   (d) SEQ ID NO:40;
   (e) SEQ ID NO:41; or
   (f) SEQ ID NO:42.

4. A tag peptide fusion protein having the isolated tag peptide according to claim 1 linked to the N or C terminus of a protein.

5. An isolated polynucleotide consisting of the nucleotide sequences encoding the isolated tag peptide according to claim 1.

6. A recombinant vector containing the polynucleotide according to claim 5.

7. A kit for expressing a tag peptide fusion protein, comprising the recombinant vector according to claim 6.

8. A purification method for proteins comprising the following steps (i) to (iv):
   (i) a step of preparing a mixture of at least one other substance and a tag peptide fusion protein having the isolated tag peptide according to claim 1 linked to a protein of interest;

(ii) a step of allowing a monoclonal antibody immobilized onto a support to act on the mixture obtained in the step (i) and to form a complex with the tag peptide fusion protein, wherein the monoclonal antibody is produced by mouse-mouse hybridoma P20.1 having accession number FERM BP-11061;

(iii) a step of washing the complex immobilized on the support; and (iv) a step of allowing a water-miscible organic solvent to act on the washed complex obtained in the step (iii) for release of the tag peptide fusion protein from the antibody, thereby purifying the fusion protein from the at least one other substance.

* * * * *